US010912287B2

(12) United States Patent
Shen et al.

(10) Patent No.: US 10,912,287 B2
(45) Date of Patent: *Feb. 9, 2021

(54) GENETICALLY MODIFIED MICE EXPRESSING HUMANIZED PD-1

(71) Applicant: Biocytogen Pharmaceuticals (Beijing) Co., Ltd, Beijing (CN)

(72) Inventors: Yuelei Shen, Beijing (CN); Yang Bai, Beijing (CN); Rui Huang, Beijing (CN); Xiaofei Zhou, Beijing (CN); Yuting Hu, Beijing (CN); Yanan Guo, Beijing (CN); Jichao Du, Beijing (CN)

(73) Assignee: Biocytogen Pharmaceuticals (Beijing) Co., Ltd, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/313,819

(22) PCT Filed: Jun. 27, 2017

(86) PCT No.: PCT/CN2017/090320

§ 371 (c)(1),
(2) Date: Dec. 27, 2018

(87) PCT Pub. No.: WO2018/001241

PCT Pub. Date: Jan. 4, 2018

(65) Prior Publication Data

US 2019/0387724 A1 Dec. 26, 2019

(30) Foreign Application Priority Data

Jun. 28, 2016 (CN) .......................... 2016 1 0487764

(51) Int. Cl.

| | |
|---|---|
| ***A01K 67/027*** | (2006.01) |
| ***G01N 33/00*** | (2006.01) |
| ***C12N 15/00*** | (2006.01) |
| ***A61D 19/04*** | (2006.01) |
| ***A61K 49/00*** | (2006.01) |
| ***C07K 14/705*** | (2006.01) |
| ***C12N 9/22*** | (2006.01) |
| ***C12N 15/11*** | (2006.01) |
| ***C12N 15/85*** | (2006.01) |

(52) U.S. Cl.

CPC .......... *A01K 67/0278* (2013.01); *A61D 19/04* (2013.01); *A61K 49/0008* (2013.01); *C07K 14/70521* (2013.01); *C12N 9/22* (2013.01); *C12N 15/11* (2013.01); *C12N 15/8509* (2013.01); *A01K 2217/072* (2013.01); *A01K 2227/105* (2013.01); *A01K 2267/0331* (2013.01); *C12N 2015/8572* (2013.01); *C12N 2310/20* (2017.05); *C12N 2800/80* (2013.01)

(58) Field of Classification Search

USPC ............................................ 800/3, 8, 18, 21

See application file for complete search history.

(56) References Cited

U.S. PATENT DOCUMENTS

| | | | |
|---|---|---|---|
| 4,683,195 | A | 7/1987 | Mullis et al. |
| 8,728,474 | B2 | 5/2014 | Honjo et al. |
| 9,834,606 | B2 | 12/2017 | Li et al. |
| 1,031,429 | A1 | 6/2019 | Shen |
| 1,045,796 | A1 | 10/2019 | Frendewey et al. |
| 2002/0115209 | A1 | 8/2002 | Liu et al. |
| 2004/0033497 | A1 | 2/2004 | Alarcon-Riquelme et al. |
| 2015/0106961 | A1 | 4/2015 | Rojas et al. |
| 2015/0366174 | A1 | 12/2015 | Burova et al. |
| 2016/0157469 | A1 | 6/2016 | Burova et al. |
| 2017/0247454 | A1 | 8/2017 | Benz et al. |
| 2019/0373868 | A1 | 12/2019 | Shen |

FOREIGN PATENT DOCUMENTS

| | | | |
|---|---|---|---|
| CN | 1113518 | | 12/1995 |
| CN | 103820454 | | 5/2014 |
| CN | 104561095 | | 4/2015 |
| CN | 104593418 | | 5/2015 |
| CN | 106604635 | | 4/2017 |
| WO | WO 2002/36789 | | 5/2002 |
| WO | WO 2004/074320 | * | 9/2004 |
| WO | WO 2015/090230 | * | 6/2015 |
| WO | WO 2015/196051 | * | 12/2015 |
| WO | WO 2016/094481 | | 6/2016 |
| WO | WO 2017/087780 | | 5/2017 |

(Continued)

OTHER PUBLICATIONS

GenBank XM_017596382, 2016.*
Schilit (Curr Protoc Hum Genet., Oct. 2016, vol. 91, 15.10.1-15.10.28).*
Harms (Curr Protoc Hum Genetics, 2014, 15.7.1-15.7.27).*
Rotte, J. Exp. & Clin. Cancer Res., 2019, vol. 38, No. 255, p. 1-12.*
Burova (Cancer Res., 2016, vol. 76, No. 14, Abstract 1484, AACR 107th Annual Meeting, 2016, Apr. 16-20, 2016, New Orleans).*
English translation of Bian CN103820454, 2014.*
Gennequin (Biochem. & Biophysical Res. Comm., 2013, vol. 441, p. 815-819).*
Aida (Genome Biol, 2015, vol. 16, No. 87, p. 1-11).*
GenBank Accession No. L27440.1, "Human PD-1 gene, complete cds," GenBank, Dec. 28, 1994, 2 pages.
GenBank Accession No. X67914.1, "M musculus PD-1 mRNA," GenBank, Jul. 26, 1993, 3 pages.

(Continued)

*Primary Examiner* — Michael C Wilson

(74) *Attorney, Agent, or Firm* — Fish & Richardson P.C.

(57) ABSTRACT

Provided is a method for preparing a PD-1 gene-modified humanized animal model. The method utilizes the CRIPSR/Cas9 technique to replace partial fragments of a mouse PD-1 gene with fragments of a human PD-1 gene using homologous recombination by constructing a targeting vector, thereby preparing a gene-modified humanized mouse. This mouse can normally express a PD-1 protein containing the functional domain of the human PD-1 protein, and can be used as an animal model for mechanism research regarding PD-1, PD-L1 and other signals, for screening regulators, and for toxicological research. The method has an important and high application value in studies on functions of the PD-1 gene and in the development of new drugs.

13 Claims, 22 Drawing Sheets

Specification includes a Sequence Listing.

(56) References Cited

FOREIGN PATENT DOCUMENTS

| | | |
|---|---|---|
| WO | WO2018001241 | 1/2018 |
| WO | WO2018041118 | 3/2018 |
| WO | WO2018041119 | 3/2018 |
| WO | WO2018041120 | 3/2018 |
| WO | WO2018041121 | 3/2018 |
| WO | WO2018068756 | 4/2018 |
| WO | WO2018086583 | 5/2018 |
| WO | WO2018086594 | 5/2018 |
| WO | WO2018121787 | 7/2018 |
| WO | WO2018177440 | 10/2018 |
| WO | WO2018177441 | 10/2018 |

OTHER PUBLICATIONS

Lute et al., "Human CTLA4 knock-in mice unravel the quantitative link between tumor immunity and autoimmunity induced by anti-CTLA-4 antibodies," Blood, American Society of Hematology, 106(9):3127-3133.

Supplementary Partial European Search Report in European Appln. No. EP 17819238, dated Nov. 21, 2019, 10 pages.

Creelan, Benjamin C. "Update on immune checkpoint inhibitors in lung cancer."Cancer Control 21.1 (2014): 80-89.

Festing et al., "Revised nomenclature for strain 129 mice," Mammalian Genome, 1999. 10:836.

Hirano et al., "Blockade of B7-H1 and PD-1 by monoclonal antibodies potentiates cancer therapeutic immunity," Cancer research. 2005, 65(3):1089-1096.

International Search Report and Written Opinion in Appln. No. PCT/CN2017/090320, dated Sep. 20, 2017, 18 pages (with English translation).

International Search Report and Written Opinion in Appln. No. PCT/CN2018/110069, dated Jan. 11, 2019, 10 pages.

Ito. M. et al., NOD/SCID/ γcnull mouse: an excellent recipient mouse model for engraftment of human cells, Blood 100 (9): 3175-3182, 2002.

Kaufmann et al.. "PD-1 and CTLA-4 Inhibitory Consignaling Pathways in HIV Infection and the Potential for Therapeutic Intervention," The Journal of Immunology, 2009, 182:5891-5897.

Kowk et al., "Pembrolizumab (Keytruda)," 2016, 2777-2789.

Palmer et al., "In vivo blockade of the PD-1 receptor suppresses HIV-1 viral loads and improves CD4+ T cell levels in humanized mice," J. Immunol., 2012, 190:211-219.

Raedler, "Keytruda (pembrolizumanb): first PD-1 inhibitory approved for previously treated unresectable or metastatic melanoma," American health & drug benefits, 2015, 8:96-100.

Topalian et al., "Safety, activity, and immune correlates of anti-PD-1 antibody in cancer," New England Journal of Medicine, 2012, 366(26):2443-2454.

Yin et al., "Delivery technologies for genome editing," Nature Reviews Drug Discovery 16.6 (2017): 387-399.

Burova et al., "Characterization of the Anti-PD-1 Antibody REGN2810 and Its Antitumor Activity in Human PD-1 Knock-In Mice," Mol Cancer Ther., May 2017, 16(5):861-870.

Baidu Tieba, "Biocytogen pd-1 Humanized Mice," https://tieba.baidu.com/p/4610326082, 2016, 10 pages (with English translation).

Klimke et al., "State-of-art humanized mouse models and the CRISPR/Cas9 technology at TaconicArtemis," Transgenic Res., 2014, 23(5):906-907.

Li, "Heritable gene targeting in the mouse and rat using a CRISPR-Cas system," Nature Biotech., 2013, 31(8):681-683.

Yoshimi et al., "ssODN-mediated knock-in with CRISPR-Cas for large genomic regions in zygotes," Nature Comm., 2016, 7(10431):1-10.

Auerbach et al., "Establishment and Chimera Analysis of 129/SvEv- and C57BL/6-Derived Mouse Embryonic Stem Cells Lines," 2000.

Bryan et al., "Implications of protein fold switching," Current comments, posted on Feb. 4, 2013, retrieved from URL <http://www.elsevierblogs.conn/currentconnnnents/?p=962>, p. 1-4.

Burova et al., "Abstract 266: Antitumor activity of REGN2810, a fully human anti-PD-1 monoclonal antibody, against MC38.Ova tumors grown in immune-competent humanized PD-1 mice," Cancer Research, 2015, 75(15):31 (Abstract only).

Burova et al., 2015, GeneSeq Accession No. BCK42308, Computer printout, pp. 268-270.

Burova et al., 2015, GeneSeq Accession No. BCK42308, Computer printout, pp. 295-297.

Guo et al., "Targeted genome editing in primate embryos," Cell Research, 2015, 25:767-768.

Khodarovich et al., "Expression of eukaryotic recombinant proteins and deriving them from the milk of transgenic animals," Applied Biochemistry and Microbiology, 2013, 49(9):711-722.

Lee et al., "Developing genetically engineered mouse models using engineered nucleases: Current status, challenges, and the way forward," Drug Discovery Today: Disease Models, 2016, 20:13-20.

Maksimenko et al., "Use of transgenic animals in biotechnology: prospects and problems," Acta Naturae, 2013, 5(1):33-46.

Maqbool et al., "The substrate-binding protein in bacterial ABC transporters: dissecting roles in the evolution of substrate specificity," 2015, Biochemical Society Transactions, 43(5):1011-1017.

Patil et al., "Transgenic animals and drug development: A review," Indian Journal of Public Health Research & Development, 2011, 2(1):106-109.

Selsby et al., "Porcine models of muscular dystrophy," ILAR Journal, 2015, 56(1):116-126.

Yang et al., "Mutant PFN1 causes ALS phenotypes and progressive motor neuron degeneration in mice by a gain of toxicity," PNAS, 2016, 113(41):E6209-E6218.

* cited by examiner

GENETICALLY MODIFIED MICE EXPRESSING HUMANIZED PD-1

CLAIM OF PRIORITY

This application is a 371 U.S. National Phase Application of PCT Application No. PCT/CN2017/090320, filed on Jun. 27, 2017, which claims the benefit of Chinese Patent Application 201610487764.7, filed on Jun. 28, 2016. The entire contents of the foregoing are incorporated herein by reference.

FIELD OF THE INVENTION

The present application relates to the field of animal genetic engineering and genetic modification, and in particular, to a method for constructing a PD-1 gene-modified humanized animal model based on the CRISPR/Cas9 technique and a use thereof in biomedicine.

BACKGROUND OF THE INVENTION

A humanized animal model refers to an animal model that carries human functional genes, cells or tissues. This model is typically used as an alternative living model for research on human diseases, and has tremendous advantages and a prospect of extensive applications in understanding pathogenesis and drug screening.

To study pathogenesis of complicated human diseases and screen effective drugs, a lot of in vivo experiments need to be performed by using ideal animal models. Mice have been one of the mostly used biological models. Considering the differences between mice and humans in physiological, pathological, and many other aspects, however, it is particularly important to construct humanized mouse models that carry human functional genes, cells or tissues. In studies on some human diseases, one method is to use humanized genetic animal models that are prepared by "placing" human genes on chromosomes of rats and mice using a method of gene modification.

At present, tumor immunotherapy is one of the most promising research directions in the field of tumor treatment. The journal Science ranked tumor immunotherapy as No. 1 of Top Ten Science Breakthroughs in 2013. Right now, studies on PD-1/PD-L1 channel inhibitors have attracted particular attention.

PD-1 (programmed death-1) is mainly expressed on the surface of T cells and preliminary B cells. Two ligands of PD-1 (PD-L1 and PD-L2) are extensively expressed in antigen-presenting cells (APCs) and others. The interaction between PD-1 and its receptors plays an important role in negative regulation of immune response. The expression of PD-L1 protein can be detected in many human tumor tissues. The micro-environment of tumor sites can induce an expression of PD-L1 on tumor cells. The expressed PD-L1 is favorable for genesis and growth of tumors, induces the apoptosis of anti-tumor T cells, and then evades the attack from an immune system. By inhibiting the binding of PD-1 and its ligands, tumor cells can be exposed to the attack of an immune system, and then the effect of killing tumor tissues and treating cancers can be achieved.

Currently, many big domestic and international companies begin to intensify the development of anti-PD-1 drugs. The most known global pharmaceutical giants are BMS and Merck & Co. Opdivo and Keytruda by the two companies have overcome melanoma and lung cancer indications. In November 2015, FDA approved the use of Opdivo on advanced renal cell carcinoma, and the critical Phase III clinical trial of Opdivo on head and neck cancer was successfully completed. The results disclosed on ASCO GI 2016 held in January 2016 indicate that these two drugs show positive therapeutic effect on ductal carcinoma and stomach cancer. At the end of 2015, Shanghai Junshi Biosciences Co., Ltd. became the first company in China with a PD-1 monoclonal antibody approved for clinical use; in January 2016, BGB-A317, a PD-1 monoclonal antibody by BeiGene (Beijing) Co., Ltd., passed the FDA review for new drug research application and was approved for clinical trials in the U.S.; on February 19, SHR-1210 (a PD-1 monoclonal antibody) for injection developed by Jiangsu Hengrui Medicine Co., Ltd. was approved for medicine clinical trial with the main indication being solid tumors; on February 22, Walvax Biotechnology issued an announcement that the application for clinical research on an anti-PD-1 monoclonal antibody product (genolimzumab injection) developed by its subsidiary Genor BioPharma Co. Ltd. was accepted, and the main potential indications thereof included various blood cancers and a variety of solid tumors like melanoma, non-small lung cancer, and renal cancer. As of March 2016, two domestic companies had PD-1 monoclonal antibody drugs approved for clinical trials, and two others were in the acceptance process.

The fierce competition among pharmaceutical companies shows the high acceptance of this type of drugs. PD-1 inhibitors could become an important benchmark in the history of medicine. The US National Cancer Institute (NCI) has listed PD-1 as the second most promising potent target in 140 cancer immunotherapy paths and molecules.

Since immunotherapy has relatively significant immunotoxicity, such as dermatitis, colitis, hypophysitis, and the like, the side effect is directly related to the degree of immune response and difficult to be avoided through dosage adjustment. A serious adverse reaction, pneumonia, has been reported for nivolumab and MK-3475, both of which are PD-1 monoclonal antibodies. Therefore, it is very important to have a strict drug screening procedure. Due to the significant difference between human physiology and animal physiology, however, experiment results obtained from animal models sometimes are not applicable to humans. As humanized animal models can "replicate" some human functions very well, this type of models is often used as alternative living models for in vivo research on human diseases. Humanized animal models have extensive applications. For example, they are applicable in fields like tumors, AIDS, infectious diseases, human degenerative diseases, and blood diseases.

Some PD-1 gene-related animal models have already been developed at present. For example, Nihimura et al. prepared BALB/c mice with PD-1 knocked out in 2001. These models were mainly used in studies on functions of the PD-1 gene and relevant disease mechanisms. Because of the tremendous value of the PD-1 gene in applications in fields of tumor and immunotherapy, the present invention is hereby provided in light of the insufficiencies and defects of the prior art, so as to make efficacy trials in early stage clinical trials more effective and improve the success rate of research and development.

SUMMARY OF THE INVENTION

An object of the present invention is to provide a PD-1 gene-modified humanized non-human mammal model.

A second object of the present invention is to provide a method for preparing the PD-1 gene-modified humanized non-human mammal model.

A third object of the present invention is to provide an application of the model.

To achieve the objects of the present invention, the following technical solution is employed:

1) constructing a targeting vector: obtaining a homology arm from genome DNA using PCR, and connecting the homology arm with an hPD-1 fragment to be introduced to the targeting vector;

2) constructing sgRNA: designing and selecting sgRNA according to the target site, connecting sgRNA to the vector plasmid, and performing in vitro transcription;

3) transferring the targeting vector and the transcribed sgRNA into embryonic cells, and transplanting the embryonic cells into animals with false pregnancy;

4) genotyping the obtained chimeric animals, screening to obtain a positive animal with successful gene knock-in; subsequently, the positive animal copulating with a wild-type animal to obtain F1 generation heterozygotes; and obtaining homozygotes after copulation among the F1 generation heterozygotes.

Based on the above technical solution, the present invention provides a PD-1 gene-modified humanized animal model, the animal is a non-primate mammal, the genome thereof contains human PD-1 gene fragments and can normally express PD-1 functional protein, and the expressed protein contains a functional domain of human PD-1 genes.

The PD-1 gene modification is a gene modification performed on the second exon of the PD-1 gene.

Furthermore, the non-primate mammal is a rodent.

Furthermore, the rodent is a mouse.

Preferably, the background of the mouse is C57BL/6.

For the PD-1 gene-modified humanized animal model according to the present invention, nucleotides 11053-11385 of its PD-1 gene are replaced by a human DNA fragment, and other mouse PD-1 regions including the transmembrane region are retained; the human DNA fragment is as shown by SEQ ID NO: 21.

In one example of the present invention, for the provided PD-1 gene-modified humanized animal model, nucleotides 11053-11385 of its PD-1 gene are replaced by a human DNA fragment, and 14/13 bp of the left and right edges of the second exon and other mouse PD-1 regions including the transmembrane region are retained; the human DNA fragment is as shown by SEQ ID NO: 21.

The present invention provides the DNA sequence of a humanized mouse PD-1 gene, and the protein encoded with the DNA sequence contains functional domains of human PD-1 proteins.

The present invention provides the DNA sequence of a humanized mouse PD-1 gene, wherein nucleotides 11053-11385 of a mouse PD-1 gene are replaced by a human DNA fragment, and 14/13 bp of each of the left and right edges of the second exon and other mouse PD-1 regions including the transmembrane region are retained; the human DNA fragment is as shown by SEQ ID NO: 21 or is a DNA fragment having 80% or higher homology with this fragment; the DNA sequence of the humanized mouse PD-1 gene contains a nucleotide sequence shown by SEQ ID NO: 14 or a DNA fragment having 80% or higher homology with the DNA sequence of the humanized mouse PD-1 gene. In one example of the present invention, the upstream and downstream primer sequences used for amplifying the DNA sequence of the humanized mouse PD-1 gene are as shown by SEQ ID NO: 22-23.

For the DNA sequence of the humanized mouse PD-1 gene, its CDS sequence is shown by SEQ ID NO: 15 or a DNA fragment having 80% or higher homology with SEQ ID NO: 15, its mRNA sequence is shown by SEQ ID NO: 16 or a DNA fragment having 80% or higher homology with SEQ ID NO: 16, and the protein sequence encoded thereby is shown by SEQ ID NO: 17 or a specific amino acid fragment thereof with unchanged functions. The present invention provides a use of the DNA sequence of a humanized mouse PD-1 gene in constructing the PD-1 gene-modified humanized animal model, wherein nucleotides 11053-11385 of the second exon of the mouse PD-1 gene are replaced by a human DNA fragment, and other mouse PD-1 regions including the transmembrane region are retained, the human DNA fragment is as shown by SEQ ID NO: 21, and the DNA sequence of the humanized mouse PD-1 gene contains a nucleotide sequence shown by SEQ ID NO: 14.

Furthermore, in a specific example of the present invention, nucleotides 11053-11385 of the second exon of the mouse PD-1 gene are replaced by a human DNA fragment, and 14/13 bp is retained for each of the left and right edges.

Furthermore, the use is to inject an in vitro transcription product containing an expression vector of the DNA sequence of the humanized mouse PD-1 gene and Cas9mRNA, and sgRNA plasmid of the second exon of the mouse PD-1 gene into a cytoplasm or nucleus of a mouse fertilized egg, and to transplant the fertilized egg into a receiving female mouse for producing the PD-1 gene-modified humanized mouse model.

The present invention provides sgRNA of the second exon of the specifically targeted mouse PD-1 gene, and its target site sequence is as shown by SEQ ID NO: 3 or SEQ ID NO: 8.

In the present invention, the upstream and downstream single stranded sequences, as shown by SEQ ID NO: 9-10, respectively, of a target site sequence as shown by SEQ ID NO: 3 are synthesized; the upstream and downstream single stranded sequences, as shown by SEQ ID NO: 11-12, respectively, of a target site sequence as shown by SEQ ID NO: 8 are synthesized.

The CRISPR/Cas9 targeting vector that contains the DNA sequence of the sgRNA falls within the protection scope of the present invention.

The present invention provides a use of the sgRNA or the CRISPR/Cas9 targeting vector in preparing a PD-1 gene-modified humanized animal model.

In the present invention, a method for preparing a PD-1 gene-modified humanized animal model is provided, the method comprising the following steps:

(1) connecting the DNA sequence, 3' homology arm and 5' homology arm of the humanized mouse PD-1 gene of the present invention to a plasmid, and constructing a homologous recombinant expression vector of the second exon of the humanized mouse PD-1 gene; the 5' homology arm is as shown by SEQ ID NO: 18, and the 3' homology arm is as shown by SEQ ID NO: 24;

(2) constructing a plasmid of sgRNA of the second exon of the mouse PD-1 gene;

(3) injecting the in vitro transcription product from the step (2), the expression vector from the step (1), and Cas9mRNA into a cytoplasm or nucleus of a mouse fertilized egg, and transplanting the fertilized egg into a receiving female mouse for producing the PD-1 gene-modified humanized mouse model.

In the step (1), the DNA of a wild-type C57BL/6 mouse genome is used as a template for PCR amplification of the 5' homology arm fragment and the 3' homology arm fragment, and the amplified primer pair sequences are as shown by SEQ ID NO: 19-20 and SEQ ID NO: 25-26, respectively; the plasmid is PV-4G.

The plasmid of sgRNA of the second exon of the mouse PD-1 gene from the step (2) is obtained by connecting the sgRNA to a pT7-sgRNA plasmid.

The present invention further provides a PD-1 gene-modified humanized animal model prepared using the above method.

The present invention provides a use of the animal model, the DNA sequence of the humanized mouse PD-1 gene, the sgRNA for the second exon of the mouse PD-1 gene, or its CRISPR/Cas9 targeting vector in preparing PD-1 or PD-L1 regulators or drugs.

The present invention provides a use of the animal model, the DNA sequence of the humanized mouse PD-1 gene, the sgRNA for the second exon of the mouse PD-1 gene, or its CRISPR/Cas9 targeting vector in research on PD-1 or PD-L1 signal mechanism.

The present invention provides a use of the animal model, the DNA sequence of the humanized mouse PD-1 gene, the sgRNA for the second exon of the mouse PD-1 gene, or its CRISPR/Cas9 targeting vector in oncological research.

The present invention further relates to sperms, eggs, fertilized eggs, embryos, progenies, tissues or cells from a gene-modified animal, research on PD-1/PD-L1 signal mechanism of the above biological material, and use in pre-clinical experiments, such as research on drug toxicity of PD-1/PD-L1 regulators and screening and development of PD-1/PD-L1 regulators.

The present invention provides a use of the animal model, the DNA sequence of the humanized mouse PD-1 gene, the sgRNA, or CRISPR/Cas9 targeting vector comprising the same in R&D of PD-1 or PD-L1 regulators or drugs, in research on PD-1 or PD-L1 signaling mechanism, and in oncological research.

The present invention provides a mouse carrying humanized and modified PD-1 genes, wherein its genome contains human PD-1 gene fragments, can normally express PD-1 functional protein, and the expressed protein contains a functional domain of human PD-1 genes.

Furthermore, for the mouse carrying humanized and modified PD-1 genes, nucleotides 11053-11385 of the second exon of its PD-1 gene are replaced by a DNA fragment of human PD-1 gene, 14/13 bp is retained for each of the left and right edges, and other mouse PD-1 regions including the transmembrane region are retained; and the human DNA fragment is as shown by SEQ ID NO: 21.

The present invention provides a use of the animal model or the mouse carrying humanized and modified PD-1 genes in preparing a multi-gene humanized animal model.

The multi-gene humanized animal model prepared using the animal model or the mouse carrying humanized and modified PD-1 genes through copulation or further with a gene editing method also falls within the protection scope of the present invention.

Furthermore, a use of the multi-gene humanized animal model in drug R&D or in oncological research falls within the protection scope of the present invention. The drugs are monoclonal antibody, bispecific antibody, or polyclonal antibody drugs, as well as other biological or chemical drugs.

The present invention further provides a cell or tissue isolated from the animal model or any mouse.

The present invention further provides a use of the animal model, mouse, cell, or tissue in R&D of PD-1 or PD-L1 regulators or drugs, in research on PD-1 or PD-L1 signaling mechanism, and in oncological research.

The present invention further provides a use of the animal model, mouse, cell, or tissue in evaluating effectiveness of targeted PD-1/PD-L1 drugs or in screening targeted PD-1/PD-L1 drugs.

The present invention further provides a use of the animal model, mouse, cell, or tissue in evaluating effectiveness of joint administration of targeted PD-1/PD-L1 drugs and other drugs or in screening combined drugs for joint administration of targeted PD-1/PD-L1 drugs and other drugs.

The present invention further provides a use of the animal model, mouse, cell, or tissue in screening regulators for human PD-1/PD-L1 signal pathway.

The present invention further provides a method for evaluating effectiveness of targeted PD-1/PD-L1 drugs, which uses the animal model, mouse, cell, or tissue to evaluate drugs.

The present invention further provides a method for evaluating effectiveness of joint administration of drugs targeting PD-1/PD-L1 combined with other drugs, which uses the animal model, mouse, cell, or tissue to evaluate combined drugs for joint administration of drugs targeting PD-1/PD-L1 combined with other drugs.

The present invention further provides a method for screening drugs targeting PD-1/PD-L1, which uses the animal model, mouse, cell, or tissue to screen drugs.

The present invention further provides a method for screening joint administration of drugs targeting PD-1/PD-L1 combined with other drugs, which uses the animal model, mouse, cell, or tissue to screen combined drugs for joint administration of drugs targeting PD-1/PD-L1 combined with other drugs.

Furthermore, the drugs targeting PD-1/PD-L1 are drugs for treating tumors.

Preferably, the drugs are monoclonal antibody, bispecific antibody, or polyclonal antibody drugs, as well as other biological or chemical drugs. The present invention has the following features: 1) for the animal model according to the present invention, the second exon of its PD-1 gene is partially and manually replaced by the second exon of human PD-1 gene in a manner of DNA sequence homologous recombination; 2) the animal model according to the present invention can express a PD-1 protein containing the functional domain of the human PD-1 protein in the animal body. The adoption of this method can minimize the impact on humanization caused by gene splicing and editing; and retain other mouse PD-1 gene functional regions including the transmembrane region, so as to avoid abnormality in mouse expression of the PD-1 protein and physiological functions related to the PD-1 protein as a result of gene humanization.

DETAILED DESCRIPTION OF THE EXAMPLES

Biochemical reagents used in examples of the present application include EcoRI, EcoRV, HindIII, KpnI, BglII enzymes purchased from NEB with the article numbers thereof being R3101M, R3195M, R3104M, R3142M, and R0144M, respectively; NucleoBond® Xtra Maxi Plus EF purchased from Macherey-Nagel with the article number being 740426; Kanamycin purchased from Amresco with the article number being 0408; Ambion in vitro transcription kit purchased from Ambion with the article number being AM1354; AIO and UCA kits purchased from Biocytogen with the article numbers being BCG-DX-004 and BCG-DX-001, respectively; Cas9mRNA was from SIGMA with the article number being CAS9MRNA-1EA; mouse colon cancer cells MC38 purchased from EK-Bioscience; *E-coli* TOP10 competent cells purchased from Tiangen with the article number being CB104-02; anti-mouse PD-1 from Biolegend with the article number being 135210; Cisplatin from Hospira Australia Pty Ltd.; mouse CD3 antibody from BD with the article number being 563123; mPD-1 PE from Biolegend with the article number being 109104; hPD-1 FITC from Biolegend with the article number being 329904; mTcRrβ PerCP from Biolegend with the article number being 109228; mCTLA-4 APC from Biolegend with the article number being 106310; and hCTLA-4 PE from Biolegend with the article number being 349906.

Example 1 Design of sgRNAs Targeting PD-1 Gene

The target sequence determines the targeting specificity of small guide RNA (sgRNA) and the efficiency of Cas9 cleavage at the target gene. Therefore, target sequence selection was important for sgRNA vector construction.

Design and synthesize a guide RNA sequence for identifying the 5'-terminal targeting site (sgRNA1 to sgRNA4) and the 3'-terminal targeting site (sgRNA5 to sgRNA8). Using mice as an example, according to the function and sequence features of the PD-1 gene, the 5'-terminal targeting site and the 3'-terminal targeting site were both on the second exon of the mouse PD-1 gene, and the target site sequence of each sgRNA on PD-1 was as follows:

```
sgRNA-1 target site sequence (SEQ ID NO: 1):
5'-agggacctccagggcccattggg-3'

sgRNA-2 target site sequence (SEQ ID NO: 2):
5'-cagaggtccccaatgggccctgg-3'

sgRNA-3 target site sequence (SEQ ID NO: 3):
5'-gtagaaggtgagggacctccagg-3'

sgRNA-4 target site sequence (SEQ ID NO: 4):
5'-ccctcaccttctacccagcctgg-3'

sgRNA-5 target site sequence (SEQ ID NO: 5):
5'-gcaccccaaggcaaaaatcgagg-3'

sgRNA-6 target site sequence (SEQ ID NO: 6):
5'-ggagcagagctcgtggtaacagg-3'

sgRNA-7 target site sequence (SEQ ID NO: 7):
5'-gttaccacgagctctgctccagg-3'

sgRNA-8 target site sequence (SEQ ID NO: 8):
5'-gcaaaaatcgaggagagccctgg-3'
```

Example 2 Screening of sgRNAs

Figure 1:
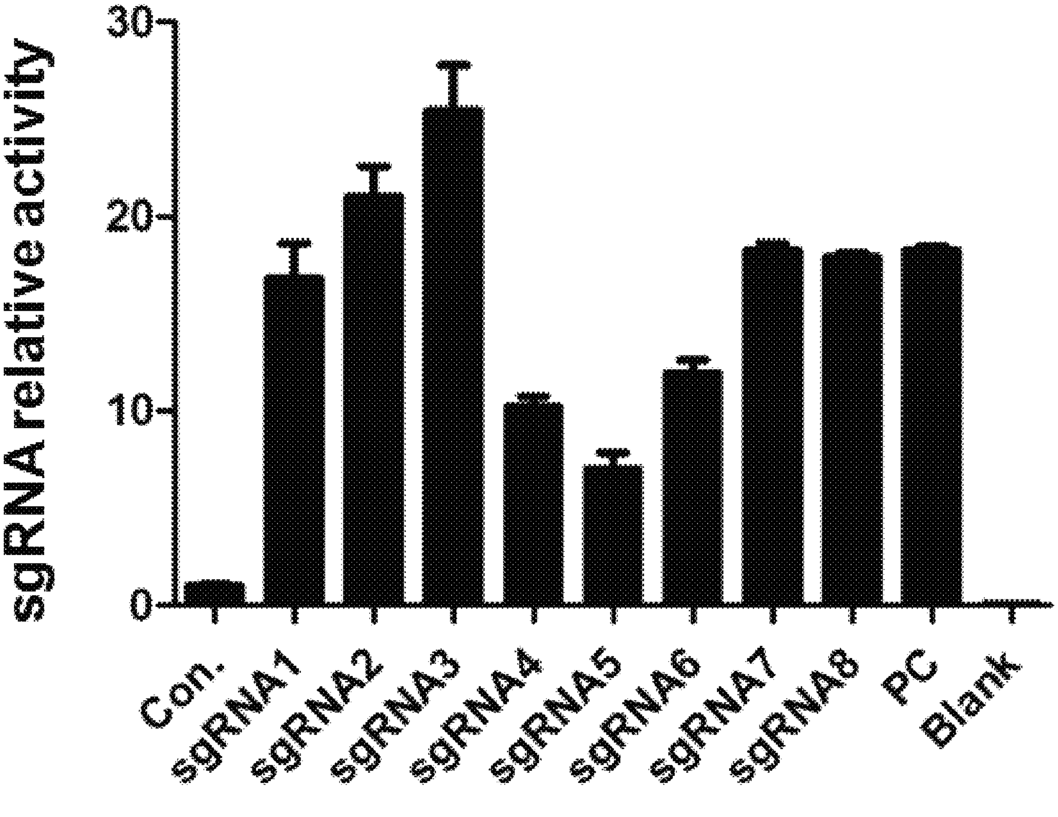
FIG. 1: activity test results for the 5'-terminal targeting site sgRNA (sgRNA1-sgRNA4) and the 3'-terminal targeting site sgRNA (sgRNA5-sgRNA8), wherein Con was a negative control, PC was a positive control, and blank was a blank control.

The UCA kit was used to detect activities of a plurality of guide sgRNAs screened from Example 1, and it can be seen from the results that the guide sgRNAs have different activities. See FIG. 1 for the detection results.

Two of them, sgRNA3 and sgRNA8, were selected therefrom for subsequent experiments.

Upstream and downstream single strands of the sgRNAs were synthesized. See Table 1:

TABLE 1

List of sgRNA3 and sgRNA8 sequences

| | |
|---|---|
| | sgRNA3 sequence |
| SEQ ID NO: 9 | Upstream: 5'-tagaaggtgagggacctcc-3' |
| SEQ ID NO: 10 | Downstream: 5'-ggaggtccctcaccttcta-3' |
| | sgRNA8 sequence |
| SEQ ID NO: 11 | Upstream: 5'-caaaaatcgaggagagccc-3' |
| SEQ ID NO: 12 | Downstream: 5'-gggctctcctcgatttttg-3' |

Example 3 Construction of pT7-sgRNA Plasmid

Figure 2:
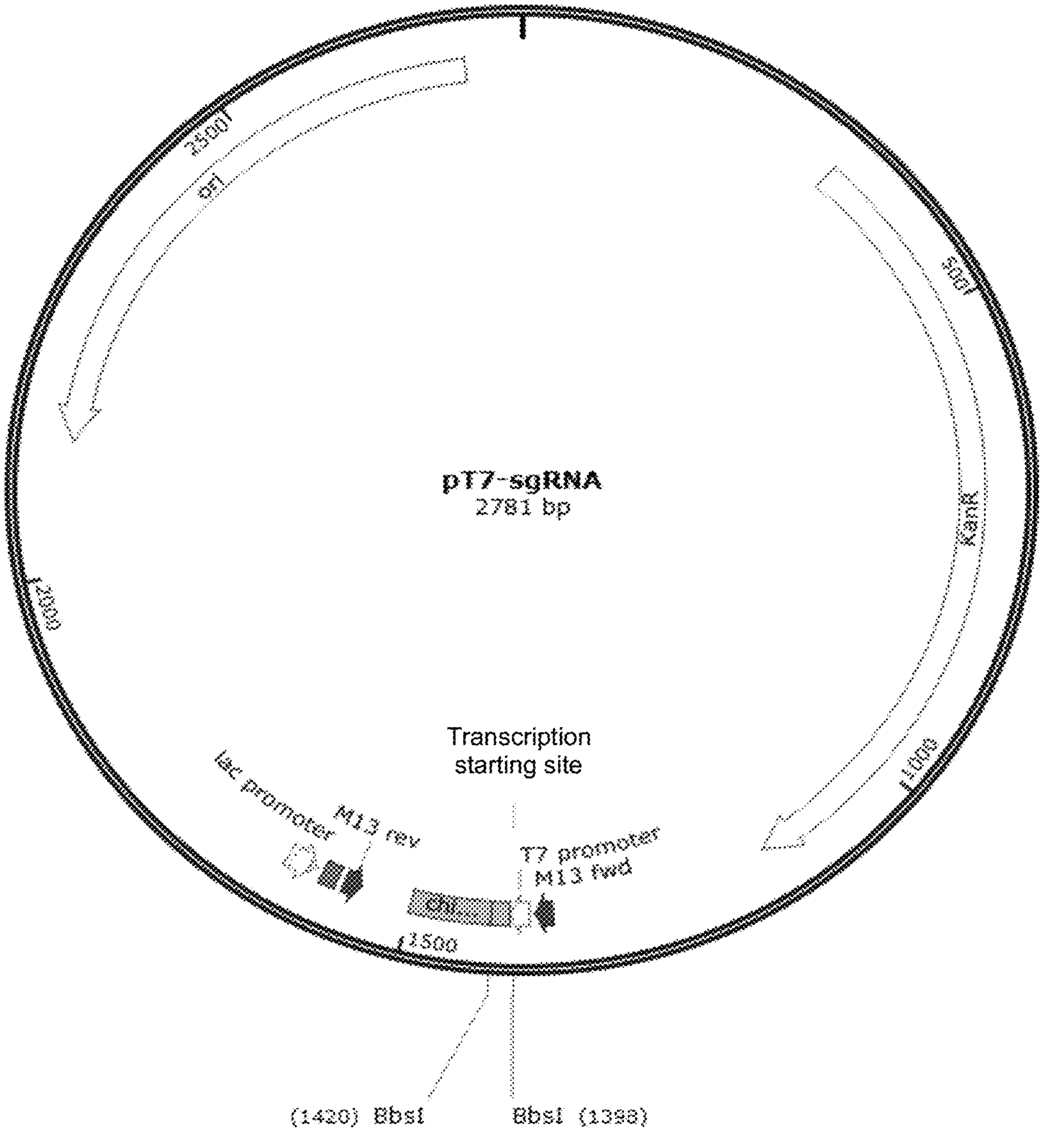
FIG. 2: a plasmid map of pT7-sgRNA.

The source of pT7-sgRNA plasmids: see FIG. 2 for the pT7-sgRNA vector map. The plasmid backbone was from Takara with the Catalog No. 3299. DNA fragments containing a T7 promoter (taatacgactcactatagg) and sgRNA scaffold were synthesized by a plasmid synthesis company (see SEQ ID NO: 13) and were connected to the skeleton vector through enzyme digestion (EcoRI and BamHI). As verified through sequencing by a professional sequencing company, the results show that the target plasmids were obtained.

Example 4 Construction of pT7-PD-3 and pT7-PD-8 Vectors

For sgRNA3 and sgRNA8 listed in Table 1, TAGG was added to the 5' ends of the upstream single strands and AAAC was added to the 5' ends of the downstream single strands. After annealing, the upstream and downstream single strands were connected to the pT7-sgRNA plasmids (the plasmid was linearized first using Bbs1), respectively, to obtain the expression vectors pT7-PD-3 and pT7-PD-8. See Table 2 for the connection reaction system:

TABLE 2

| Connection reaction system | |
|---|---|
| sgRNA annealing product | 1 μL (0.5 μM) |
| pT7-sgRNA vector | 1 μL (10 ng) |
| T4 DNA Ligase | 1 μL (5 U) |
| 10xT4 DNA Ligase buffer | 1 μL |
| 50% PEG4000 | 1 μL |
| $H_2O$ | Add to 10 μL |

The reaction conditions were as follows: connect at room temperature for 10 to 30 min, transfer into 30vL it TOP10 competent cells, then take 200vL it for coating onto a Kan resistant plate, culture at 37° C. for at least 12 h, select 2 clones for inoculation into an LB medium having Kan resistance (5 ml), and shake to culture at 37° C. and 250 rpm for at least 12 h.

Randomly select clones for sequencing verification by a sequencing company, and select expression vectors pT7-PD-3 and pT7-PD-8 with correct connection for subsequent experiments.

Example 5 Sequence Design

Nucleotides 11053-11385 of the second exon of the mouse PD-1 gene (Gene ID: 18566) were replaced by a human DNA fragment (SEQ ID NO: 21), and the ultimately obtained DNA sequence of the modified humanized mouse PD-1 (chimeric PD-1 DNA) was shown by SEQ ID NO: 14. SEQ ID NO: 14 only lists the DNA sequence of the modified portion, wherein the 219-551 bp region was a human fragment.

According to the above operation, a human DNA fragment was replaced onto the second exon of the mouse PD-1 gene to ultimately obtain a humanized mouse. Specifically, the CDS sequence and mRNA sequence of the humanized mouse PD-1 were shown by SEQ ID NO: 15 and SEQ ID NO: 16, respectively; for SEQ ID NO: 15 (869 bp), the sites 91-423 were a human fragment, and for SEQ ID NO: 16 (1972 bp), the sites 154-486 were a human fragment; the human/mouse chimeric PD-1 protein sequence was as shown by SEQ ID NO: 17, wherein the 31-141 bp region was a human fragment.

Example 6 Vector Construction

According to the above experimental scheme, upstream primers of 3 homologous recombinant fragments, matching downstream primers, and relevant sequences were designed. Specifically, the DNA of a wild-type C57BL/6 mouse genome was used as a template for PCR amplification to obtain a 5' homology arm fragment and a 3' homology arm fragment; the DNA of a human genome was used as a template for PCR amplification to obtain a human DNA fragment.

The 5' homology arm (1770 bp): the nucleotide of the site 94041502-94043271 (SEQ ID NO:18) with an NCBI login ID being NC 000067.6, the upstream primer (SEQ ID NO:19), and the downstream primer (SEQ ID NO:20). The human DNA fragment (333 bp): the nucleotide of the site 241852634-241852966 (SEQ ID NO:21) with an NCBI login ID being NC 000002.12, the upstream primer (SEQ ID NO:22), and the downstream primer (SEQ ID NO:23). The 3' homology arm (1733 bp): the nucleotide of the site 94039436-94041168 (SEQ ID NO:24) with an NCBI login ID being NC_000067.6, the upstream primer (SEQ ID NO:25), and the downstream primer (SEQ ID NO:26).

The 5' homology arm fragment, the 3' homology arm fragment, and the human DNA fragment were connected, via the AIO kit, to the TV-4G plasmid provided with the kit, to ultimately obtain the vector TV-PD.

Example 7 Vector Verification

Figure 3:
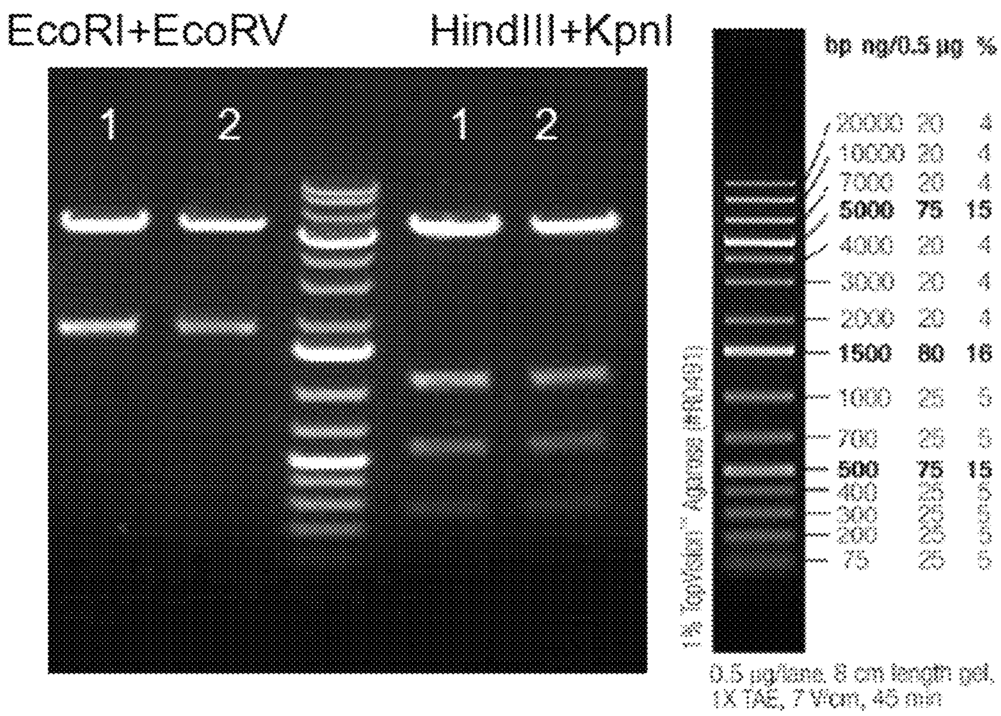
FIG. 3: results of enzyme digestion and electrophoresis of TV-PD plasmid, 1 and 2 in the figure representing 2 TV-PD plasmid, respectively.

Two TV-PD clones in Example 6 were randomly selected, 2 groups of restriction endonucleases were used for enzyme digestion verification on the clones, wherein EcoRI+EcoRV should have 1812 bp+5527 bp, and HindIII+KpnI should have 270 bp+574 bp+1091 bp+5704 bp. See FIG. 3 for the enzyme digestion results. The enzyme digestion results of plasmids 1 and 2 all meet the expectation, indicating that the plasmids having these two numbers were verified to be correct by the enzyme digestion verification. Here, No. 2 plasmid was verified to be correct via sequencing by a sequencing company.

Example 8 Microinjection and Embryo Transfer

Fertilized egg of C57BL/6 mice were taken, a microinjector was used to inject the in vitro transcription product of pT7-PD-3 and pT7-PD-8 plasmids prepared in Example 4 (using the Ambion in vitro transcription kit for transcription according to the instructions), Cas9mRNA and TV-PD plasmids that were premixed into a cytoplasm or nucleus of a mouse fertilized egg. Microinjection of embryos was performed according to the method in the "Mouse Embryo Operation Experiment Manual ($3^{rd}$ Ed)," and the fertilized egg after injection were transferred into a culture medium for a short period of culture. Then, they were transplanted into the oviduct of a receiving female mouse to produce gene-modified humanized mice. Founder mice having the C57BL/6 background (i.e., the Founder mice that were the F0 generation) were obtained. The obtained mice were subjected to hybridization and auto-copulation to increase the population and establish a stable mouse breed. The immune node humanized mice obtained using this method were named as B-hPD-1.

Example 9 Identification of Gene-Modified Humanized Mice

1. F0 Generation Genotyping

Two pairs of primers were used, respectively, to perform PCR analysis on the tail genome DNA of the F0 generation B-hPD-1 mice obtained in Example 8. Regarding positions of the primers, L-GT-F was at the left side of the 5' homology arm, R-GT-R was at the right side of the 3' homology arm, and R-GT-F and L-GT-R were both on the second exon. The 5' end upstream primer L-GT-F (SEQ ID NO:27), and the downstream primer L-GT-R (SEQ ID NO:28). The 3' end upstream primer R-GT-F (SEQ ID NO:29), and the downstream primer R-GT-R (SEQ ID NO:30). The PCR reaction system (20 μL) was shown in Table 3:

TABLE 3

| | |
|---|---|
| 10x buffer | 2 μL |
| dNTP (2 mM) | 2 μL |
| $MgSO_4$ (25 mM) | 0.8 μL |
| Upstream primer (10 μM) | 0.6 μL |
| Downstream primer (10 μM) | 0.6 μL |
| Tail genome DNA | 200 ng |
| KOD-Plus-(1 U/μL) | 0.6 μL |

The PCR amplification reaction conditions were shown in Table 4:

TABLE 4

| Temperature | Time | Number of cycles |
|---|---|---|
| 94° C. | 5 min | 1 |
| 94° C. | 30 sec | 15 |
| 67° C. (−0.7° C./cycle) | 30 sec | |
| 68° C. | 1 kb/min | |
| 98° C. | 10 sec | 25 |
| 56° C. | 30 sec | |
| 68° C. | 1 kb/min | |
| 68° C. | 10 min | 1 |
| 4° C. | 10 min | 1 |

Figure 4:
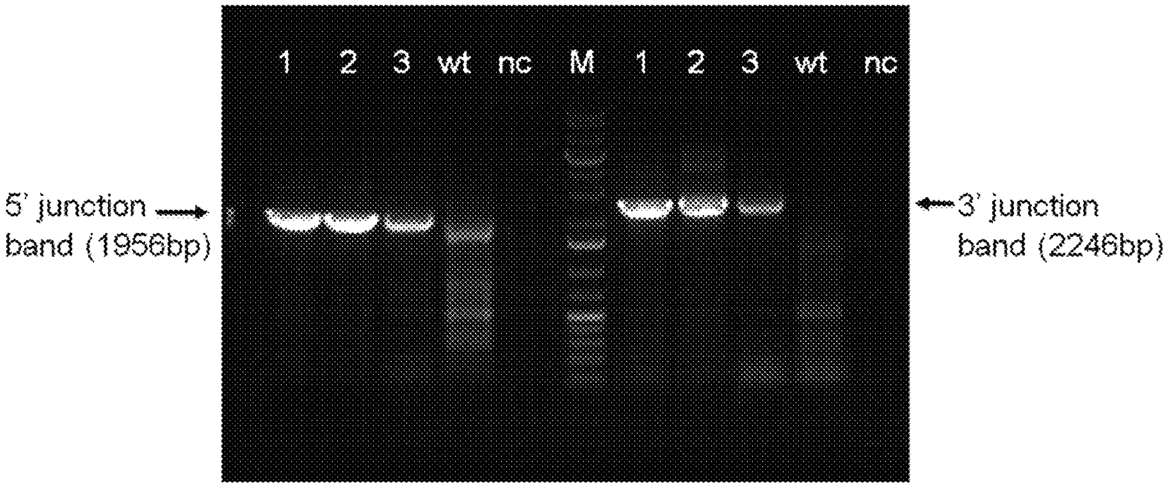
FIG. 4: PCR identification results of founder mice tails, wherein wt was a wild-type mouse, nc was a negative control, M was a mark, and 1, 2, and 3 in the figure represent tail PCR identification results of three F0 mice in Example 9.

If the insertion position of the recombinant vector was correct, there should be only one PCR band, the length of the 5' end primer product should be 1956 bp, and the length of the 3' end primer product should be 2245 bp. A total of 3 out of the obtained 24 F0 generation mice were identified to be positive mice. The PCR identification of the 3 mice tails were shown in FIG. 4.

2. F1 Generation Genotyping

Figure 5:
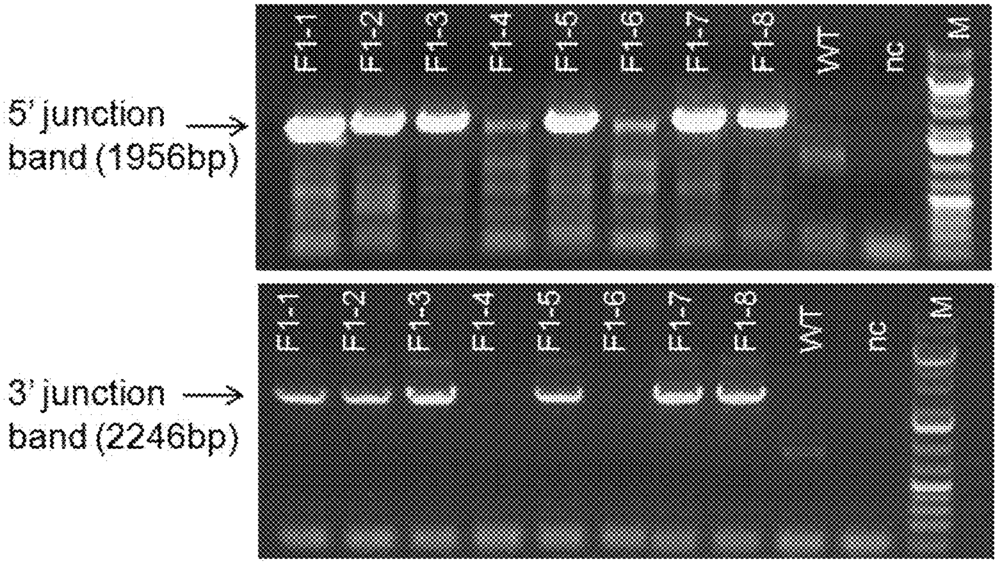
FIG. 5: PCR results of F1 generation mice, wherein WT was a wild-type mouse, nc was a negative control, and M was a mark.

The F0 generation mice identified to be positive were subjected to copulation with wild-type mice to obtain F1 generation mice. PCR analysis was performed on the tail genome DNA of the F1 generation mice. The PCR system, reaction conditions, and primers re the same as those for the F0 generation genotyping. See FIG. 5 for PCR results of the F1 generation mice, which indicates that 6 F1 generation mice were positive mice with specific numbers of F1-1, F1-2, F1-3, F1-5, F1-7, and F1-8.

Furthermore, the Southern blot method was used to determine whether there was random insertion in the 6 mice determined by PCR to be positive (F1-1, F1-2, F1-3, F1-5, F1-7, and F1-8). The genomic DNA was extracted from the mouse tail KpnI and BglII enzymes were selected to digest the genomes, respectively, the digestion products were transferred to membrane and hybridized. The probes P1 and P2 were on the outside of the 3' homology arm and the humanized fragment, respectively. The probe synthesis primers were P1-F (SEQ ID NO:31), P1-R (SEQ ID NO:32); P2-F (SEQ ID NO:33), P2-R (SEQ ID NO:34), respectively.

The genetically engineered mice that have been successfully prepared produce, via probe hybridization, bands of 2.7 kb or 3.7 kb, respectively, while the wild-type C57BL/6 mouse genome only has bands of 7.3 kb or 3.7 kb with no production of hybrid bands.

Figure 6:
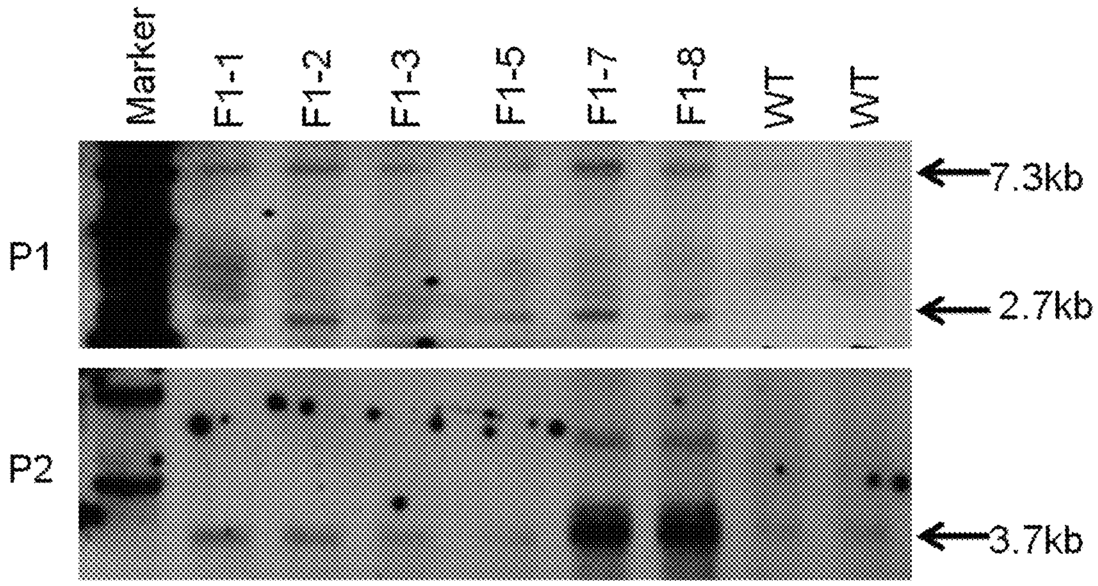
FIG. 6: Southern blot results of F1 generation mice, wherein M was a mark and WT was wild type.

The experimental results show that the sizes of hybrid bands all consistent with the expectation, proving that 4 mice were positive hybrid mice with no random insertion and numbers of F1-1, F1-2, F1-3, and F1-5, respectively; it was shown through Southern blot that 2 mice with numbers of F1-7 and F1-8 have random insertion. See FIG. 6 for the Southern blot test results. This shows that the method according to the present invention can construct B-hPD-1 humanized genetically engineered mice can have stable generations and have no random insertion.

3. Protein Identification

Figure 7:
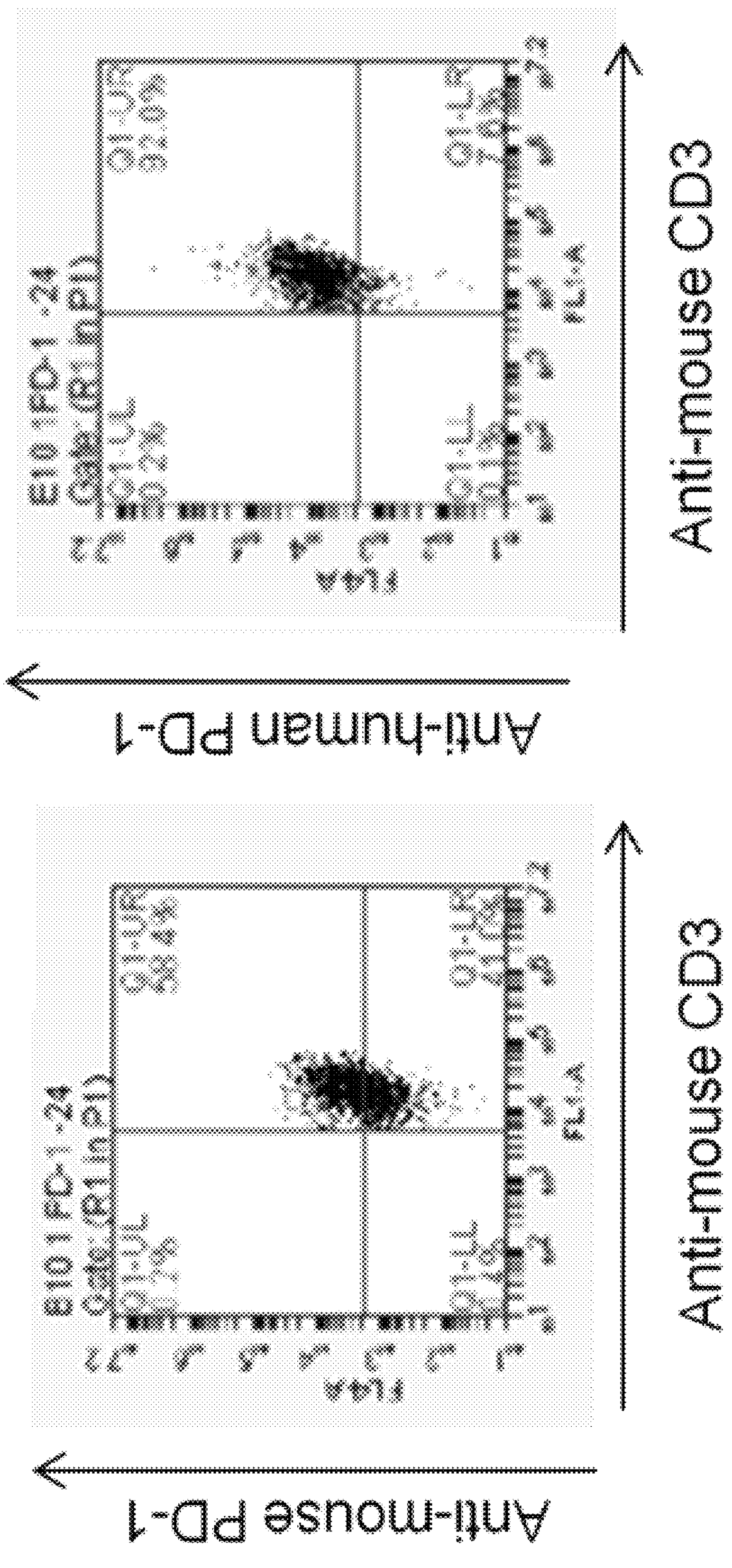
FIG. 7: flow cytometry results of the PD-1 gene-modified humanized hybrid mouse.

The F1 generation mice obtained in Example 8 were taken, their T lymphocytes (CD3+) were taken, which were subjected to flow cytometry with anti-mouse PD-1 and anti-human PD-1 antibodies. From the flow cytometry results (FIG. 7), it can be seen that the percent of the double-positive cells obtained by staining the two antibodies anti-human PD-1 and anti-mouse CD3 was 92%, indicating that the PD-1 gene-modified humanized mouse obtained using this method can express humanized PD-1 proteins.

Furthermore, the F1 generation mice obtained in Example 8 were subjected to mutual copulation to obtain F2 generation PD-1 gene humanized homozygotes. One PD-1 gene humanized homozygote (8 week old) was selected, one wild-type C57BL/6 mouse was taken as a control, 7.5 μg mouse CD3 antibody was administered to the mice through intraperitoneal injection, and after 24 h, the mice were subjected to euthanasia through neck break. The spleens were collected and grinded. The ground samples were then passed through 70 μm cell mesh, the filtered cell suspensions were centrifuged and the supernatants were discarded; the erythrocyte lysis solution was added for lysis of 5 min, and then PBS solution was added to neutralize the lysis reaction. The solution was centrifuged again and the supernatants were discarded. The cells were washed once with PBS, then subjected to FACS detection and RT-PCR detection, respectively.

Figure 8:
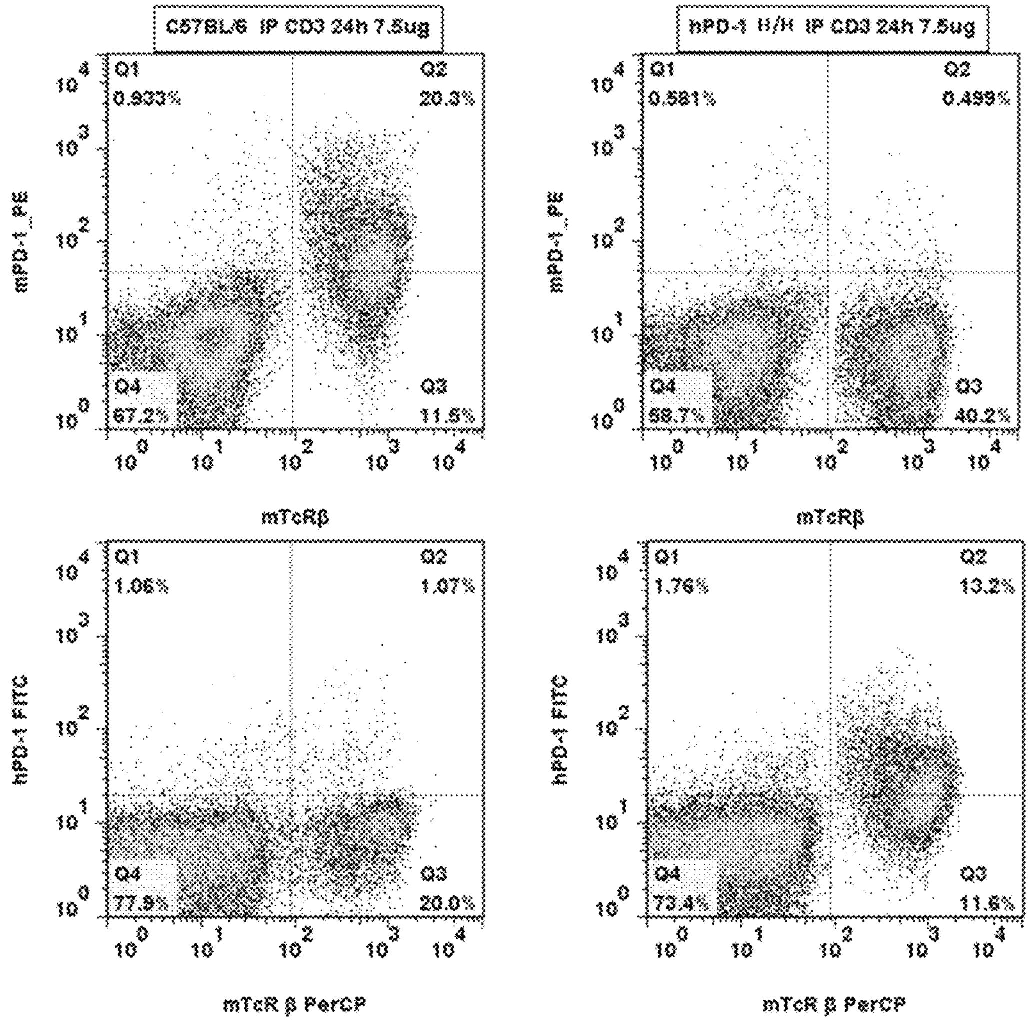
FIG. 8: flow cytometry results, wherein wild-type C57BL/6 mice and B-hPD-1 homozygous mice were taken, their T-cells in spleens were activated through the anti-mouse CD3 antibody, respectively, then the anti-mouse PD-1 antibody mPD-1PE (FIGs. A and B) and the anti-human PD-1 antibody hCD47 FITC (FIGs. C and D) were used for cell labeling; it can be seen through detection and analysis with a flow cytometer that: compared with the control group (FIGs. A and B), cells that express the human PD-1 protein can be detected in the spleens of the B-hPD-1 homozygous mice; while in the spleens of the C57BL/6 mice, no cells that express the human PD-1 protein were detected.

The FACS detection: the anti-mouse PD-1 antibody mPD-1 PE and the anti-mouse T-cell surface antibody mTcRβ, as well as the anti-human PD-1 antibody hPD-1 FITC and the anti-mouse T-cell surface antibody mTcRβ, were used simultaneously for staining T-cell extracellular proteins, and after the cells were cleaned with PBS, flow cytometry was performed to detect protection expression. The flow cytometry results (FIG. 8) show that compared with the C57BL/6 mice unstimulated and with T-cells in spleens activated through stimulation by the mouse CD3 antibody, cells that express the humanized PD-1 protein can be detected in the spleens of the humanized mice for the humanized PD-1 antibody; while in the spleens of the C57BL/6 control mice, no cells that express the humanized PD-1 protein were detected.

The RT-PCR detection: the total RNA of spleen cells was extracted from wild-type C57BL/6 mice and B-hPD-1 homozygous mice, and a reverse transcription kit was used for reverse transcription to cDNA.

Primers: mPD-1 RT-PCR F3: (SEQ ID NO:35) and mPD-1 RT-PCR R3: (SEQ ID NO:36) were used to amplify a mouse PD-1 fragment with a size of 297 bp;

Primers hPD-1 RT-PCR F3 (SEQ ID NO:37) and hPD-1 RT-PCR R3 (SEQ ID NO:38) were used to amplify a humanized PD-1 fragment with a size of 297 bp.

The PCR reaction system was 20 μL, and the reaction conditions were as follows: 95° C., 5 min; (95° C., 30 sec; 60° C., 30 sec; 72° C., 30 sec, 35 cycles); 72° C., 10 min; keeping temperature constant at 4° C. GAPDH was used as an internal control.

Figure 9:
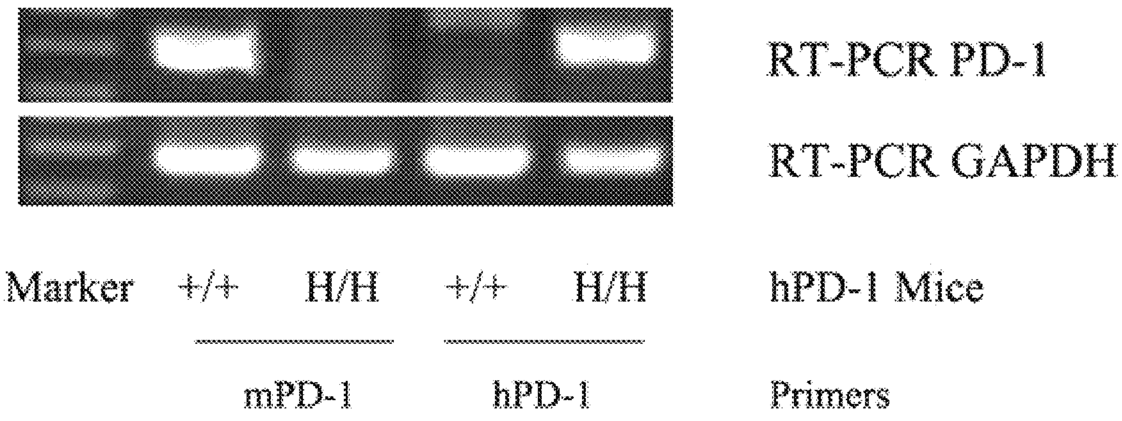
FIG. 9: RT-PCR detection results, wherein +/+ was a wild-type C57BL/6 mouse, H/H was a B-hPD-1 homozygous mouse, and GAPDH was an internal control.
Figure 10:
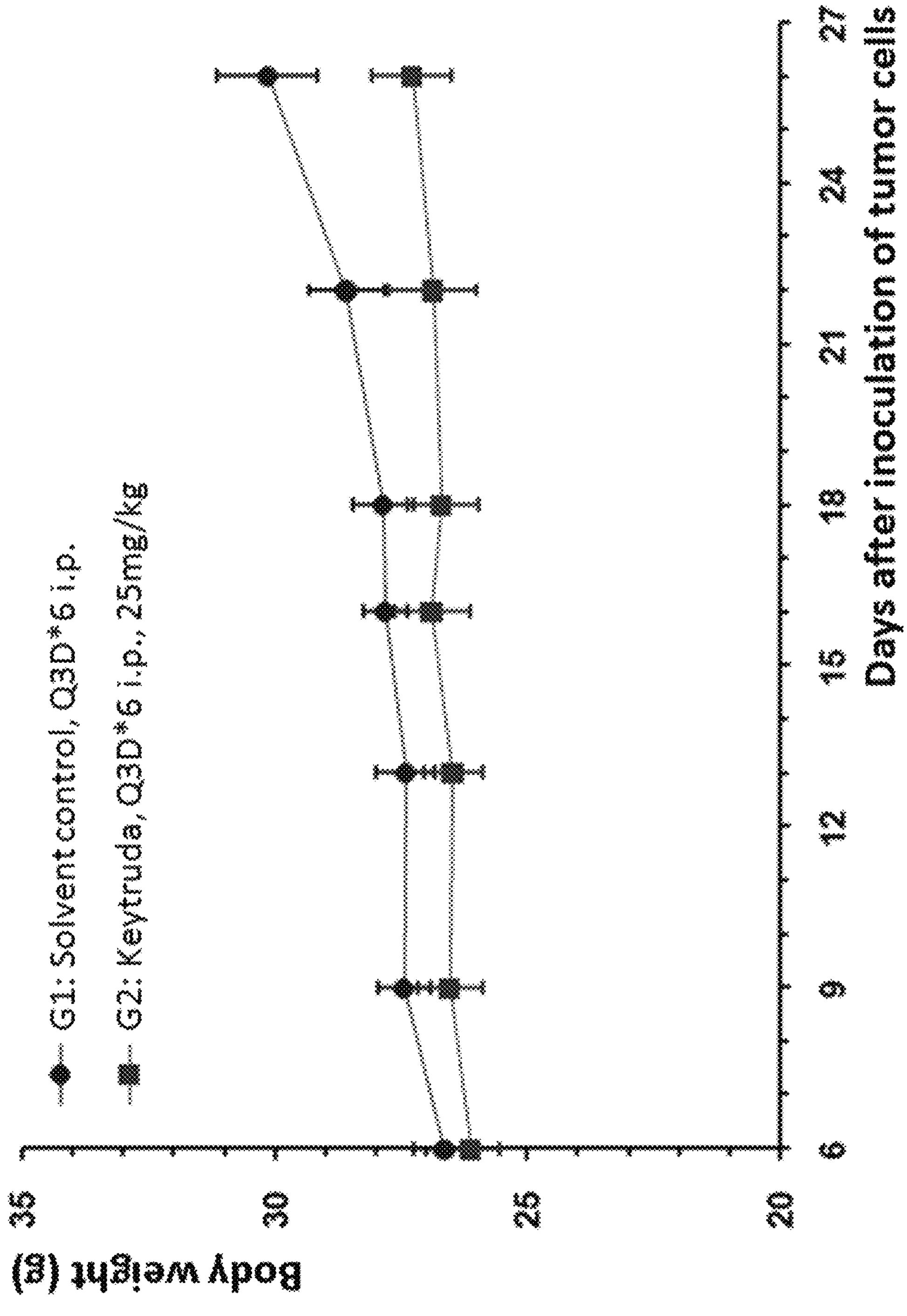
FIG. 10: mouse colon cancer cells MC38 were transplanted into B-hPD-1 mice, and the human PD-1 antibody Keytruda was used for anti-tumor efficacy test, and there was no significant difference in average weight increase between the G1 control group and G2 Keytruda treatment group.
Figure 11:
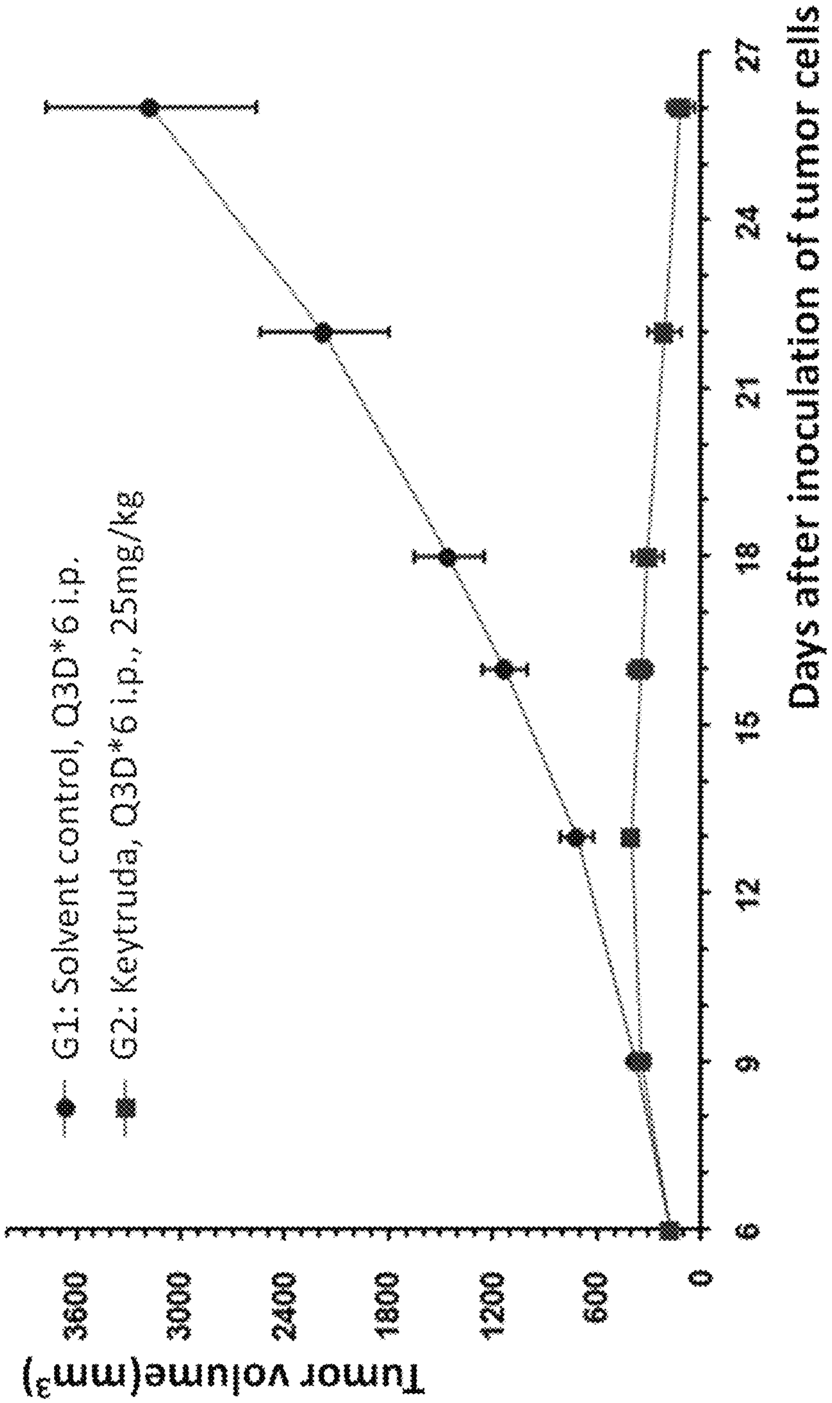
FIG. 11: mouse colon cancer cells MC38 were transplanted into B-hPD-1 mice, and the human PD-1 antibody Keytruda was used for anti-tumor efficacy test, the average volume of tumors in experimental animals in the G2 treatment group was obviously smaller than that of the G1 control group, and the difference was significant.
Figure 12:
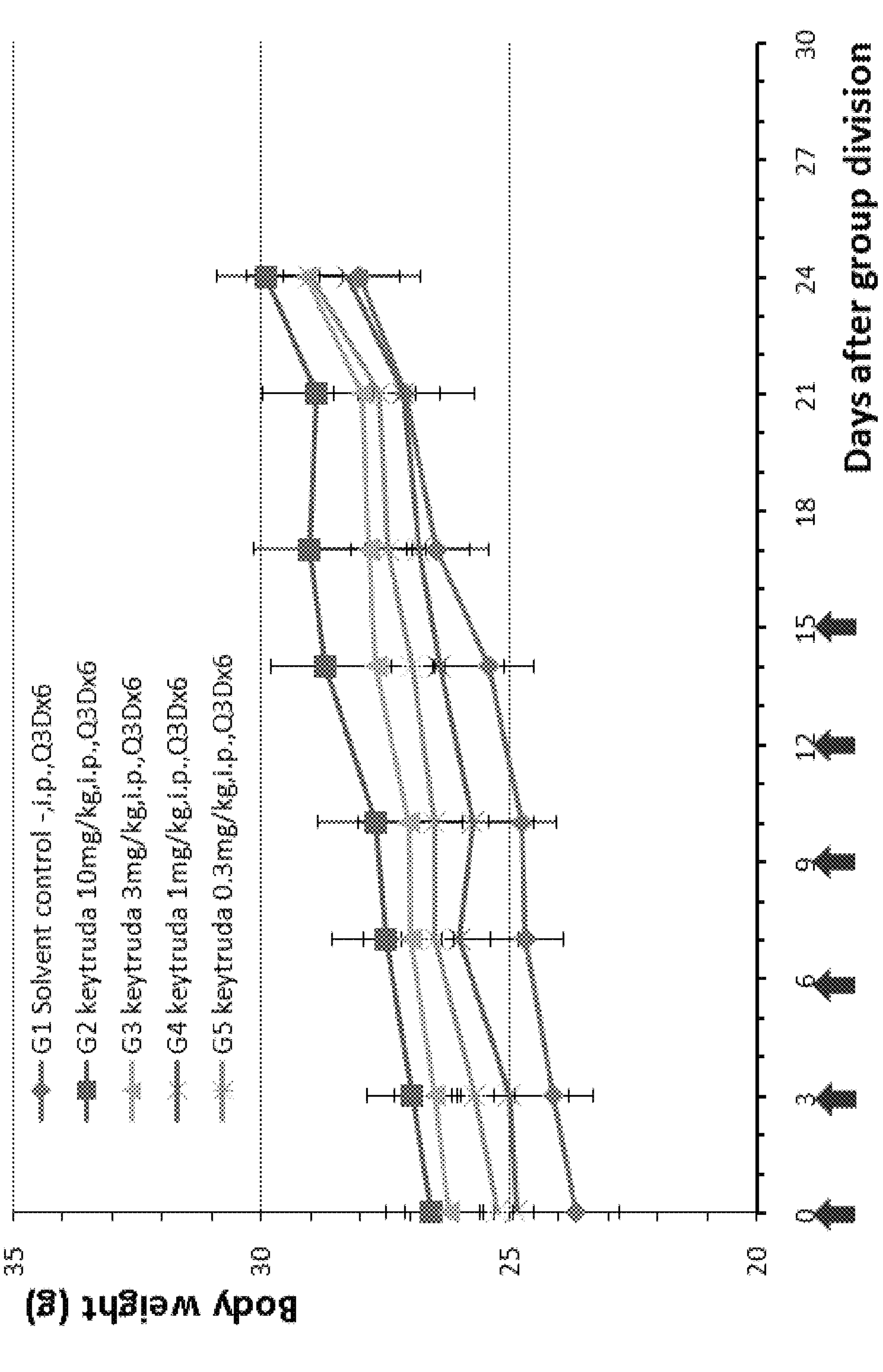
FIG. 12: mouse colon cancer cells MC38 were transplanted into B-hPD-1 mice, and different doses of the human PD-1 antibody Keytruda were used for anti-tumor efficacy tests (0.3 mg/kg, 1 mg/kg, 3 mg/kg, and 10 mg/kg), and there was no significant difference in average weight increase among experimental animals in the G1-G5 groups.
Figure 13:
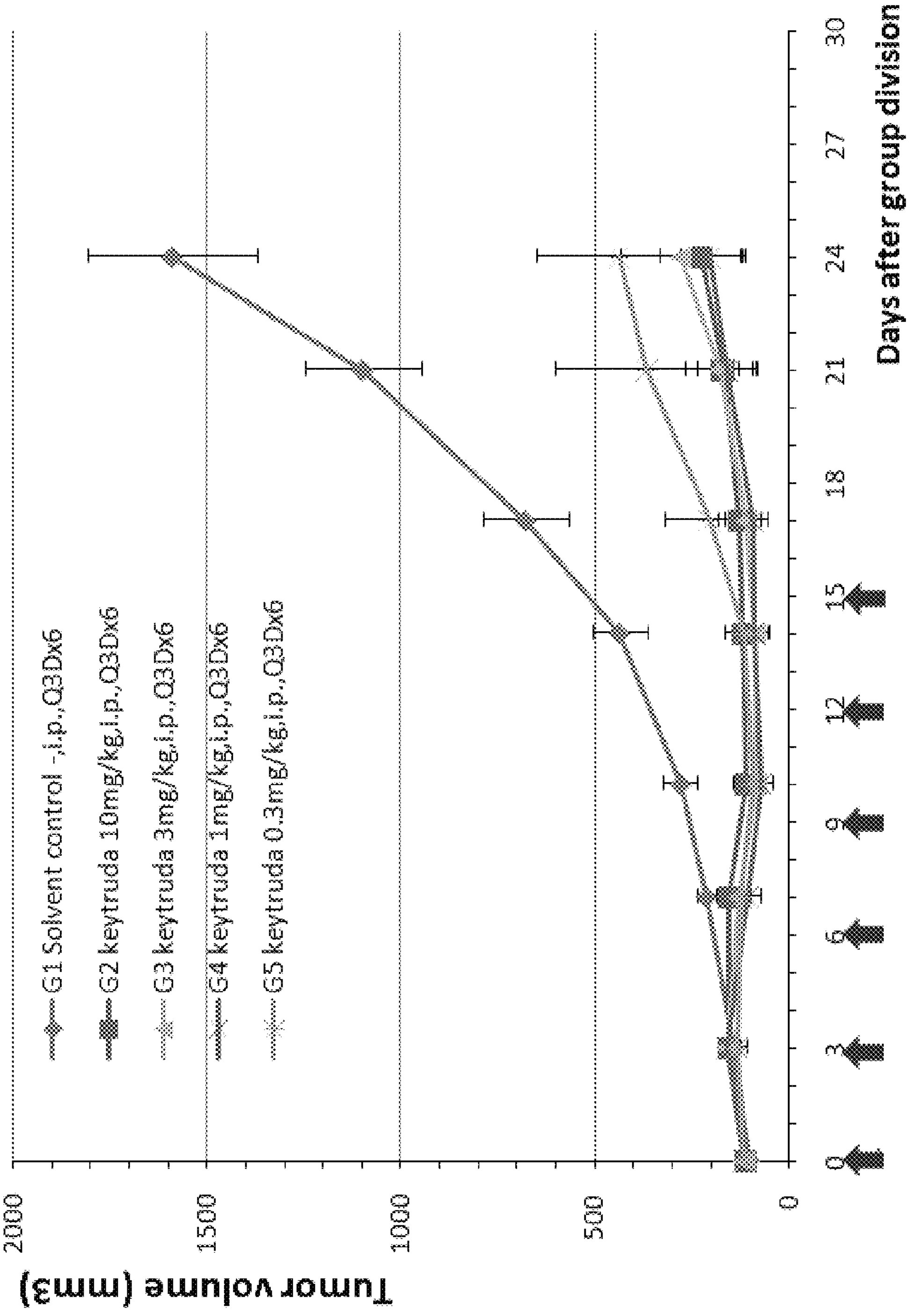
FIG. 13: mouse colon cancer cells MC38 were transplanted into B-hPD-1 mice, and different doses of the human PD-1 antibody Keytruda were used for anti-tumor efficacy tests (0.3 mg/kg, 1 mg/kg, 3 mg/kg, and 10 mg/kg), the average volume of tumors in experimental animals in the G2-G5 groups was obviously smaller than that of the G1 control group, and the difference was significant.
Figure 14:
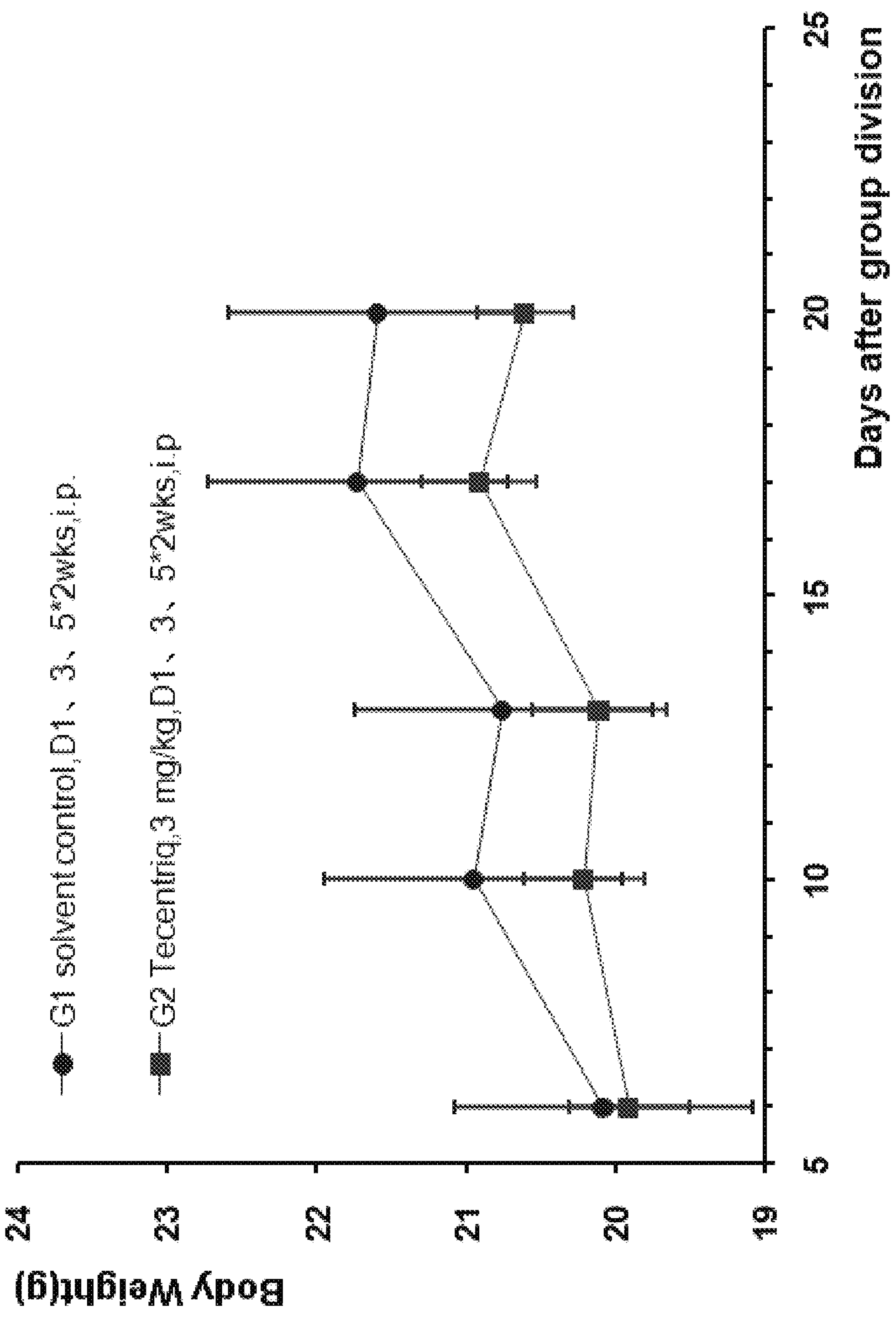
FIG. 14: the modified mouse colon cancer cells MC38-hPDL1 (the PDL1 gene humanized MC38 cells) were transplanted into B-hPD-1 mice, and the human PD-L1 antibody Tecentriq was used for anti-tumor efficacy test, and there was no significant difference in average weight increase between experimental animals in the test group and the control group.
Figure 15:
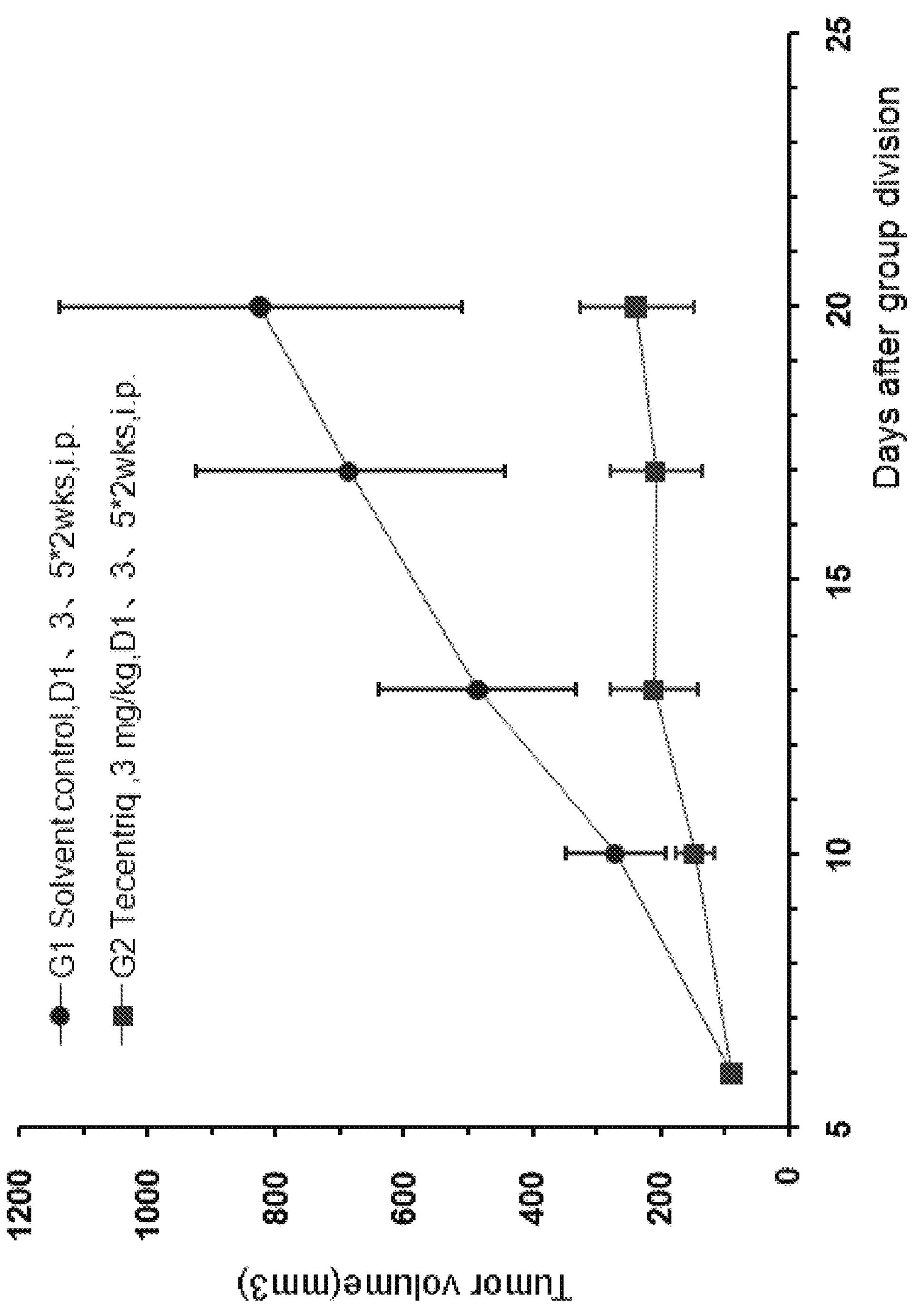
FIG. 15: the modified mouse colon cancer cells MC38-hPDL1 were transplanted into B-hPD-1 mice, and the human PD-L1 antibody Tecentriq was used for anti-tumor efficacy test, the average volume of tumors in experimental animals in the treatment group was obviously smaller than that of the control group, and the difference was significant.
Figure 16:
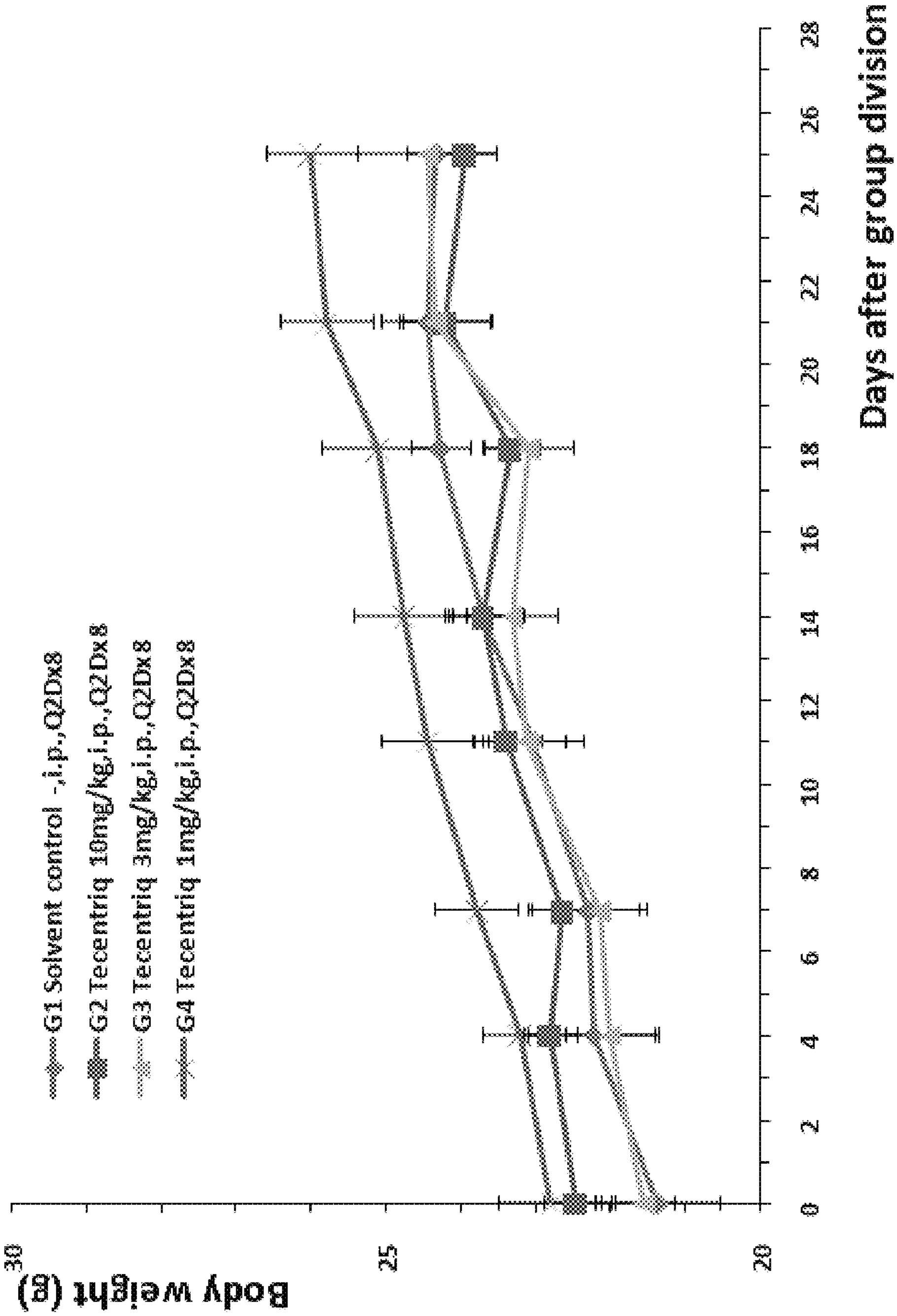
FIG. 16: the modified mouse colon cancer cells MC38-hPDL1 were transplanted into B-hPD-1 mice, and different doses of the human PD-L1 antibody Tecentriq were used for anti-tumor efficacy tests (3 mg/kg and 10 mg/kg), and there was no significant difference in average weight increase among experimental animals in the G1-G4 groups.
Figure 17:
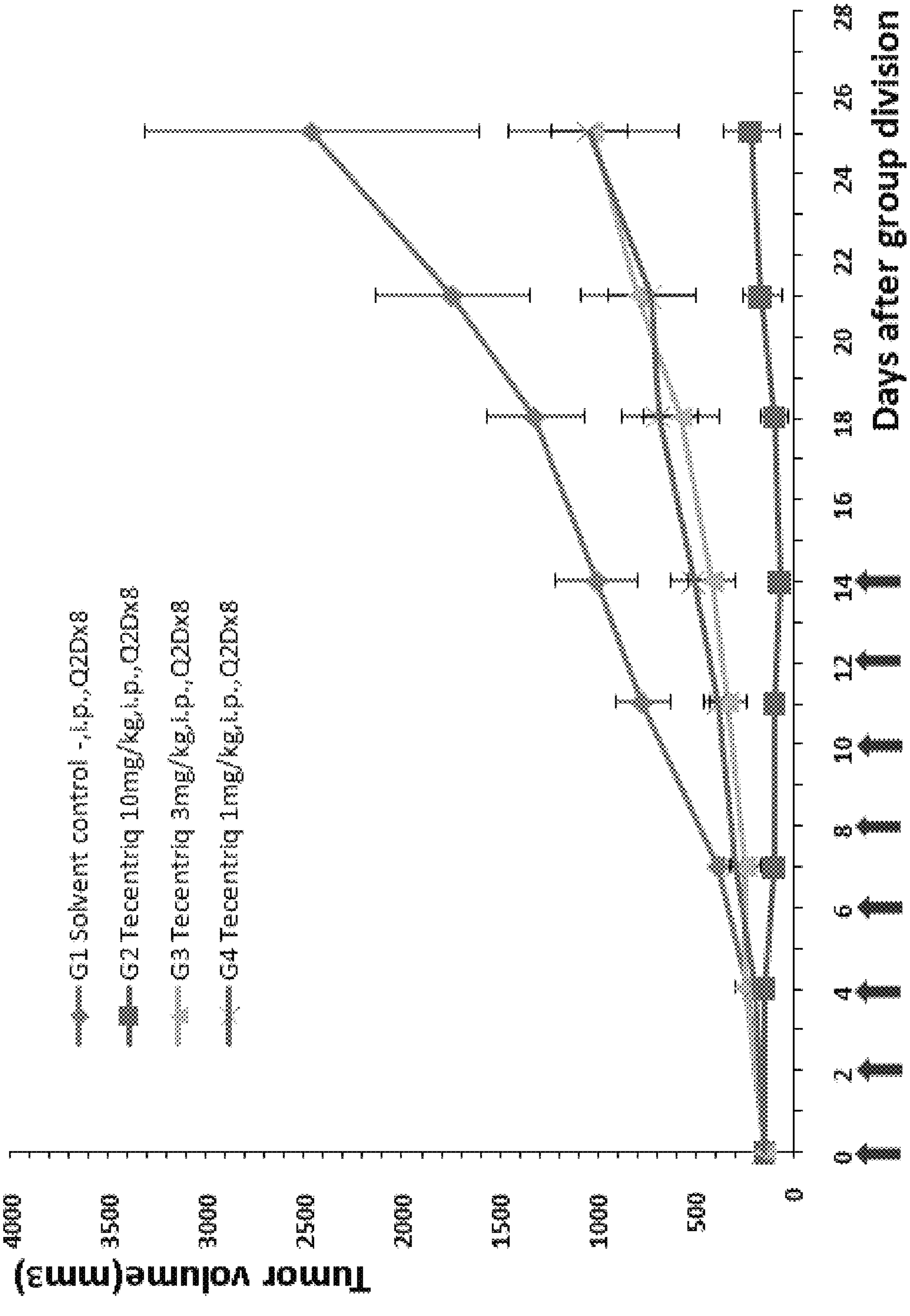
FIG. 17: the modified mouse colon cancer cells MC38-hPDL1 were transplanted into B-hPD-1 mice, and different doses of the human PD-L1 antibody Tecentriq were used for anti-tumor efficacy tests (3 mg/kg and 10 mg/kg), the average volume of tumors in experimental animals in the G2-G4 groups was obviously smaller than that of the G1 control group, and the difference was significant.

The experimental results show (FIG. 9) that mRNA expression of the mouse PD-1 can be detected in the activated cells of wild-type C57BL/6 mice, and mRNA expression of the humanized PD-1 can be detected in the activated cells of B-hPD-1 homozygous mice.

Example 10 In Vivo Efficacy Verification on the B-hPD-1 Gene Humanized Animal Model In this Example, 2 drugs for human PD-1/PD-L1 signal channels on the market that have been extensively verified were selected, which were Keytruda (pembrolizumab, a humanized monoclonal antibody) from Merck & Co. and Tecentriq (Atezolizumab, a fully humanized monoclonal antibody) from Genentech under Roche.

B-hPD-1 homozygous mice (4-6 weeks old) were taken, mouse colon cancer cells MC38 or modified MC38-hPDL1 (i.e., PD-L1 gene humanized MC38 cells) were subcutaneously inoculated. When the tumor volume was about 100 $mm^3$, the mice were randomly divided into a control group or a treatment group. For the treatment group, one of the above 2 antibodies was randomly selected and administered at different dosages (0.3-25 mg/kg), and the same volume of a blank solvent was injected for the control group. The tumor volume was measured twice a week and the body weight were measured for each mouse. Moreover, euthanasia was performed when the tumor volume of a single mouse reached 3000 $mm^3$. The specific experiment scheme was as follows:

Experiment 1 Keytruda antibody efficacy pre-experiment (n=6/group): after subcutaneous inoculation of MC38 cells to mice ($5\times10^5$/100 μL PBS), the anti-human PD-1 antibody Keytruda was administered to the treatment group at 25 mg/kg through intraperitoneal injection, and the same volume of a blank solvent was injected for the control group; the administration frequency was one administration per 3 days for a total of 6 administrations;

Experiment 2 Keytruda antibody efficacy experiments at different dosages: after subcutaneous inoculation of MC38 cells to mice ($5\times10^5$/100 μL PBS), the anti-human PD-1 antibody Keytruda was administered to the treatment group (n=6/group) through intraperitoneal injection at different dosages (0.3-10 mg/kg), and the same volume of a blank solvent was injected for the control group (n=10/group); the administration frequency was one administration per 3 days for a total of 6 administrations;

Experiment 3 Tecentriq antibody efficacy pre-experiment (n=7/group): subcutaneous inoculation of MC38-PDL1 ($5\times10^5$/100 μL PBS), the anti-human PD-1 antibody Tecentriq was administered to the treatment group at 3 mg/kg through intraperitoneal injection, and the same volume of a blank solvent was injected for the control group; the administration frequency was one administration per week for a total of 2 weeks;

Experiment 4 Tecentriq antibody efficacy experiments at different dosages (n=5/group): subcutaneous inoculation of MC38-PDL1 ($2\times10^5$/100 μL PBS), the anti-human PD-1 antibody Tecentriq was administered to the treatment group through intraperitoneal injection at 1-10 mg/kg, and the same volume of a blank solvent was injected for the control group; the administration frequency was one administration per 2 days for a total of 8 administrations;

Main data and analytical results of all experiments were listed in Tables 5, 6, 7, and 8, specifically comprising tumor volumes at the time of group division and at 10-25 days after group division, tumor volumes when the experiments end, situation of mice survival, situation of tumor-free mice, Tumor Growth Inhibition Value ($TGI_{TV}$), and statistical difference (P values) in mouse weights and tumor volumes between mice in the treatment group and the control group.

Overall, the animals have good health conditions in the experiments of all groups. At the end of all experiments, all the animals in all groups have gained weight. There was no significant difference in weight throughout the entire experiment period between all the treatment groups and control groups (FIGS. 10, 12, 14, and 16). In terms of the tumor measurements (FIGS. 11, 13, 15, and 17), however, tumors were growing continuously in the experiment period for all mice in the control groups. Compared with the control groups thereof, all the treatment groups have the volume of tumors shrunk to different degrees and/or disappears. Therefore, the treatment by either of the two drugs for human PD-1/PD-L1 signal channels on the market has significantly inhibited the growth of tumors in the mice.

Each experiment was specifically evaluated and analyzed. In Experiment 1 (see Table 5), all mice in the control group and the treatment group survive at the experiment end-point (Day 26) and had normal weight gains. Compared with the control group, the treatment group does not have a significant difference in animal weight, indicating that the animals have good tolerance against Keytruda. Tumors were growing continuously in the experiment for all mice in the control group, while at the experiment end-point, 2 of the 6 mice in the treatment group have tumors disappeared. The average tumor volume of the control group was 3168±606 $mm^3$, while the average tumor volume of the treatment group was 111±77 $mm^3$. All mice in the treatment group have a tumor volume obviously smaller than that of the control group, and the difference was significant ($p<0.05$), and $TGI_{TV}$ was 102%. Therefore, it was proven that according to the administration manner, the anti-human PD-1 antibody Keytruda has a significant inhibitory effort on tumors inside B-hPD-1 mice ($TGI_{TV}$>60%), has good capabilities of treating and inhibiting tumor growth, does not have obvious toxicity on the animals, and has good safety.

TABLE 5

| Experiment 1 | Tumor volume (mm3) Day 6 | Day 18 | Day 26 | Survival situation | Tumor free situation | $TGI_{TV}$ % | P values Weight | Tumor volume |
|---|---|---|---|---|---|---|---|---|
| Control group | 169 ± 16 | 1450 ± 202 | 3168 ± 606 | 100% | 0/6 | N/A | N/A | N/A |
| Treatment group | 169 ± 24 | 302 ± 86 | 111 ± 77 | 100% | 2/6 | 102 | 0.05 | 0.0005 |

In Experiment 2 (see Table 6), all mice in the control group and the treatment groups survive at the experiment end-point (Day 32, which was Day 24 after group division) and had normal weight gains. Compared with the control group, the treatment groups do not have a significant difference in animal weight ($p>0.05$), indicating that the animals have good tolerance against Keytruda. Similar to Experiment 1, tumors were growing continuously in the experiment for all mice in the control group, while at the experiment end-point, 7 of all the 24 mice in the treatment groups have tumors disappeared. At the experiment end-point, the average tumor volume of the control group was 1589±652 $mm^3$, while the average tumor volume of the treatment group was 223±270 $mm^3$, 277±397 $mm^3$, 201±186 $mm^3$, and 437±515 $mm^3$ at doses of 10 mg/kg, 3 mg/kg, 1 mg/kg, and 0.3 mg/kg, respectively. All mice in the treatment groups have a tumor volume obviously smaller than that of the control group, and the difference was significant ($p<0.05$) compared with the tumor volume of the control group. Overall, the optimal therapeutic effect was achieved after 3 weeks of administration. After the administration was stopped, obvious tumor growth occurs in the treatment groups having low dosage. $TGI_{TV}$ was 92.4%, 89.0%, 94.0%, and 78.2%, respectively, indicating that the anti-human PD-1 antibody Keytruda has a significant inhibitory effort on tumors ($TGI_{TV}$>60%) and shows different therapeutic effects inside B-hPD-1 mice at different dosages.

TABLE 6

| Experiment 2 | | Tumor volume ($mm^3$) Day 8 | Day 22 | Day 32 | Survival situation | Tumor free situation | $TGI_{TV}$ % | P values Weight | Tumor volume |
|---|---|---|---|---|---|---|---|---|---|
| Control group | | 100 ± 7 | 435 ± 210 | 1589 ± 652 | 10/10 | 0/10 | N/A | N/A | N/A |
| Treatment groups | 10 mg/kg | 110 ± 28 | 117 ± 111 | 223 ± 270 | 6/6 | 2/6 | 92.4 | 0.104 | 2.6E−04 |
| | 3 mg/kg | 113 ± 25 | 88 ± 94 | 277 ± 397 | 6/6 | 2/6 | 89.0 | 0.310 | 0.001 |
| | 1 mg/kg | 112 ± 27 | 89 ± 86 | 201 ± 186 | 6/6 | 2/6 | 94.0 | 0.678 | 1.8E−04 |
| | 0.3 mg/kg | 113 ± 28 | 115 ± 116 | 437 ± 515 | 6/6 | 1/6 | 78.2 | 0.259 | 0.002 |

In Experiment 3 (see Table 7), all mice in the control group and the treatment group survive at the experiment end-point (Day 20) and had normal weight gains. Compared with the control group, the treatment group does not have a significant difference in animal weight ($p>0.05$), indicating that the animals have good tolerance against Tecentriq. Tumors were growing continuously in the experiment for all mice in the control group, but at this dosage, there was no mouse cured in the treatment group (i.e., no mice have tumors disappeared). At the experiment end-point, the average tumor volume of the control group was 824±315 $mm^3$, while the average tumor volume of the treatment group was 237±89 $mm^3$. All mice in the treatment group have a tumor volume obviously smaller than that of the control group, and $TGI_{TV}$ was 79.7%. Therefore, it was proven that according to the administration manner, the anti-human PD-1 antibody Tecentriq has a significant inhibitory effort on tumors inside B-hPD-1 mice ($TGI_{TV}$>60%), has strong capabilities of inhibiting tumor growth, does not have obvious toxicity on the animals, and has good safety.

TABLE 7

| Experiment 3 | Tumor volume (mm3) Day 6 | Day 17 | Day 20 | Survival situation | Tumor free situation | $TGI_{TV}$ % | P values Weight | Tumor volume |
|---|---|---|---|---|---|---|---|---|
| Control group | 89 ± 6 | 685 ± 241 | 824 ± 315 | 7/7 | 0/7 | N/A | N/A | N/A |
| Treatment group | 88 ± 8 | 208 ± 72 | 237 ± 89 | 7/7 | 0/7 | 79.7 | 0.19 | 0.098 |

In Experiment 4 (see Table 8), all mice in the control group and the treatment groups survive at the experiment end-point (Day 33, which was Day 24 after group division) and have gained weight. Compared with the control group, the treatment groups do not have a significant difference in animal weight ($p>0.05$), indicating that the animals have good tolerance against Tecentriq. Similar to Experiment 3, tumors were growing continuously in the experiment for all mice in the control group, while at the experiment end-point, 3 of all the 15 mice in the treatment groups have tumors disappeared. At the experiment end-point, the average tumor volume of the control group was 2464±1914 $mm^3$, while the average tumor volume of the treatment groups was 219±326 $mm^3$, 1028±963 $mm^3$, and 1044±432 $mm^3$ at doses of 10 mg/kg, 3 mg/kg, and 1 mg/kg, respectively. All mice in the treatment groups have a tumor volume obviously smaller than that of the control group. $TGI_{TV}$ was 97.2%, 93.7%, and 61.2%, respectively, indicating that the anti-human PD-1 antibody Tecentriq has a significant inhibitory effort on tumors ($TGI_{TV}$>60%) at different dosages, and higher doses have better therapeutic effects. Therefore, it was proven that the anti-human PD-1 antibody Tecentriq has different therapeutic effects inside B-hPD-1 mice.

TABLE 8

| Experiment 4 | | Tumor volume ($mm^3$) Day 8 | Day 22 | Day 33 | Survival situation | Tumor free situation | $TGI_{TV}$ % | P values Day 8 | Day 22 |
|---|---|---|---|---|---|---|---|---|---|
| Control group | | 147 ± 23 | 1008 ± 469 | 2464 ± 1914 | 5/5 | 0/5 | N/A | N/A | N/A |
| Treatment groups | 10 mg/kg | 153 ± 62 | 68 ± 75 | 219 ± 326 | 5/5 | 3/5 | 97.2 | 0.498 | 0.032 |
| | 3 mg/kg | 147 ± 38 | 418 ± 268 | 1028 ± 963 | 5/5 | 0/5 | 93.7 | 0.907 | 0.172 |
| | 1 mg/kg | 144 ± 31 | 506 ± 289 | 1044 ± 432 | 5/5 | 0/5 | 61.2 | 0.051 | 0.144 |

The above research results show that the two human PD-1/PD-L1 antibodies that have been extensively used have significant inhibitory and/or eliminating effect on growth of tumors inside B-hPD-1 mice. Therefore, it was proven that the humanized PD-1 animal model can be used to evaluate in vivo the effectiveness of drugs targeting PD-1/PD-L1 and to evaluate therapeutic effects of targeting PD-1/PD-L1.

Example 11 Application of the B-hPD-1 Gene Humanized Animal Model in Efficacy of the Combined Use of Drugs Clinical research has proven that chemotherapy drugs have significant effect on a variety of solid tumors in human body, and have features like broad anti-tumor spectrum, strong effect, synergistic effect with a variety of anti-tumor drugs with no cross resistance. Joint administration of monoclonal antibodies for chemotherapy of tumors was a method that has been extensively used clinically. In this Example, the representative human PD-1 antibody Keytruda and the human PD-L1 antibody Tecentriq were administered combined with the first-line chemotherapy drug Cisplatin to prove that the B-hPD-1 mice can be used for research on the joint administration of the inhibitors for human PD-1/PD-L1 signal channels and other drugs.

B-hPD-1 homozygous mice (4-6 weeks old) were taken, $5\times10^5$ mouse colon cancer cells MC38-hPDL1 were subcutaneously inoculated at right side (the same as Example 10). When the tumor volume was about 100 $mm^3$, the mice were randomly divided into 6 control groups or treatment groups (n=7/group). For the treatment group, one or two of the above 3 drugs were randomly injected, the dosages were 0.1-10 mg/kg, and a blank solvent was injected for the control group. The tumor volume was measured and the mice were weighed twice a week. Moreover, euthanasia was performed when the tumor volume of a single mouse reached 3000 $mm^3$. The specific administration or administration combination, dosage, administration manner and frequency were listed in Table 9.

TABLE 9

| Group | Drug | Dose/administiation manner/frequency |
|---|---|---|
| G1 | blank solvent | intraperitoneal injection: once per 3 days, a total of 6 times |
| G2 | Cisplatin | 10 mg/kg: intravenous push: once per week, a total of 1 week |
| G3 | Keytruda | 0.1 mg/kg: intraperitoneal injection: once per 3 days, a total of 6 times |
| G4 | Cisplatin + Keytruda | 10 mg/kg: intravenous push: once per week, a total of 1 week 0.1 mg/kg: intraperitoneal injection: once per 3 days, a total of 6 times |
| G5 | Tecentriq | 1 mg/kg: intraperitoneal injection: once per 2 days, a total of 8 times |

TABLE 9-continued

| Group | Drug | Dose/administiation manner/frequency |
|---|---|---|
| G6 | Cisplatin + Tecentriq | 10 mg/kg: intravenous push: once per week, a total of 1 week 1 mg/kg: intraperitoneal injection: once per 2 days, a total of 8 times |

Figure 18:
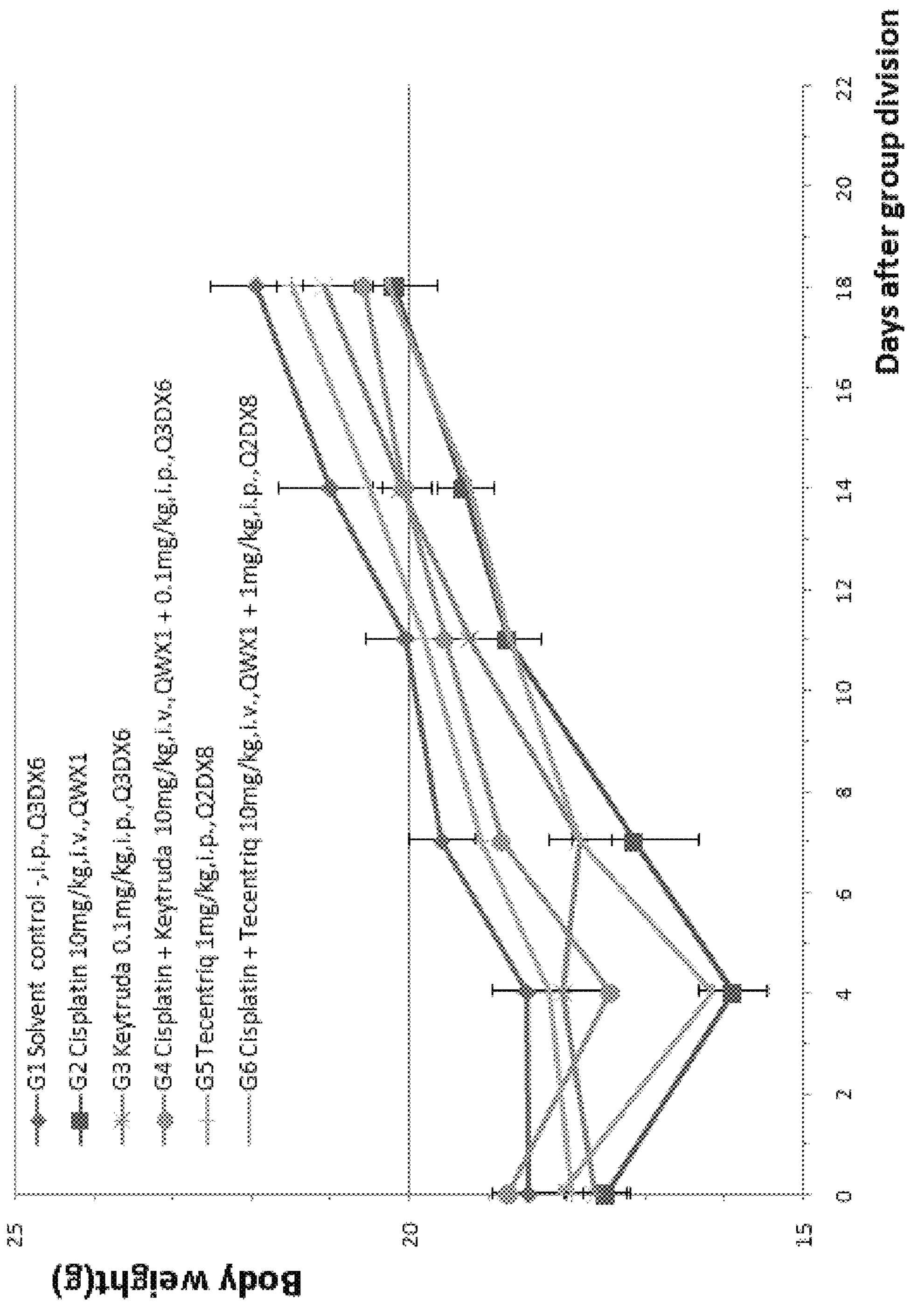
FIG. 18: the modified mouse colon cancer cells MC38-hPDL1 were transplanted into B-hPD-1 mice, and one or two of Cisplatin, Keytruda, and Tecentriq were used for anti-tumor efficacy test, and there was no significant difference in average weight increase among experimental animals in the G1-G4 groups.
Figure 19:
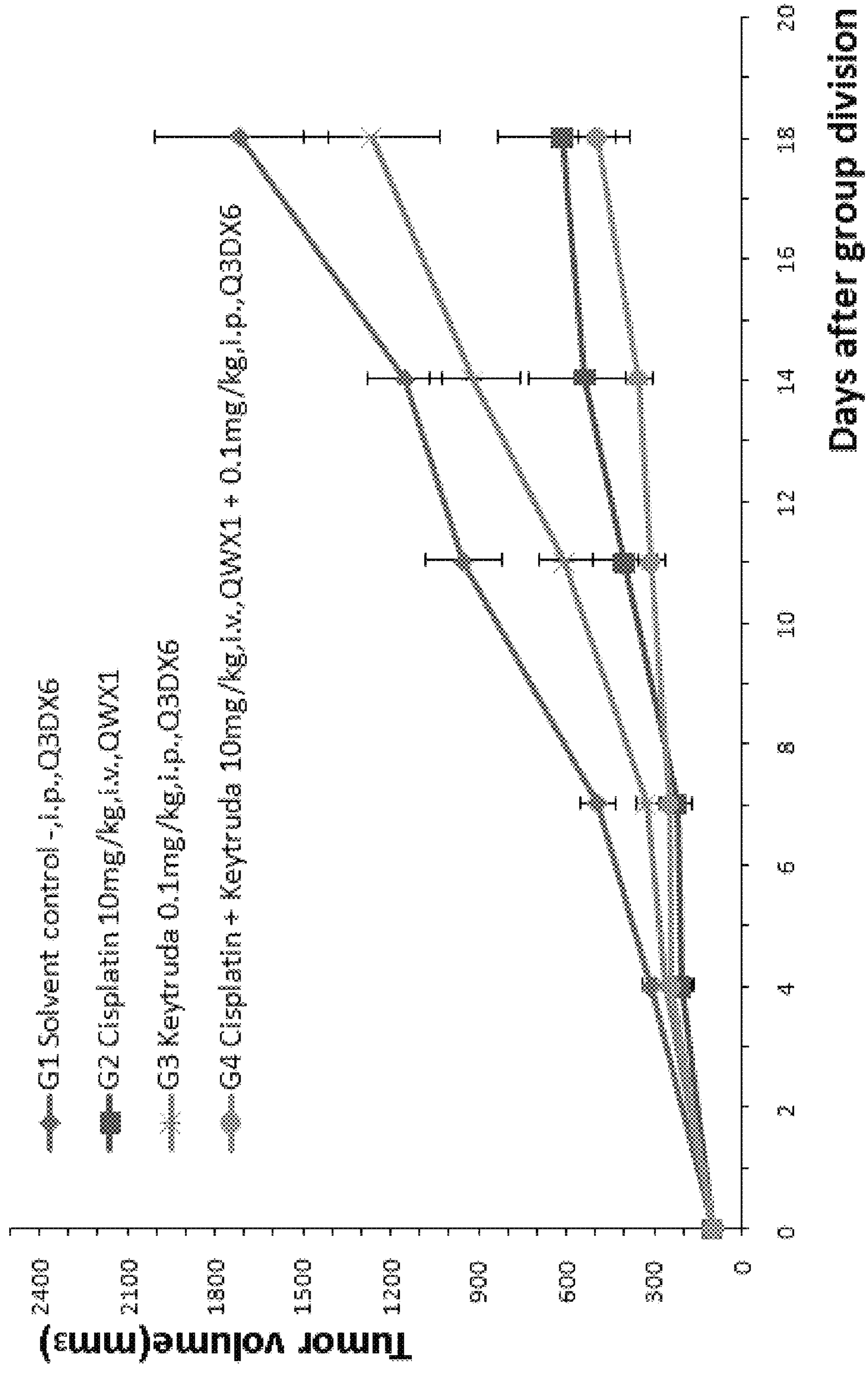
FIG. 19: the modified mouse colon cancer cells MC38-hPDL1 were transplanted into B-hPD-1 mice, and Cisplatin, Keytruda, and their combination were used for anti-tumor efficacy tests; the average volume of tumors in experimental animals in the G2-G6 treatment groups was obviously smaller than that of the control group, and the volume of tumors in mice in the Cisplatin combined with Keytruda group (G4) was significantly smaller than that of mice in the treatment group only using Cisplatin (G2) or the treatment group only using Keytruda (G3), indicating that the therapeutic effect of combination was superior to the therapeutic effect of separate administration of Cisplatin or Keytruda.
Figure 20:
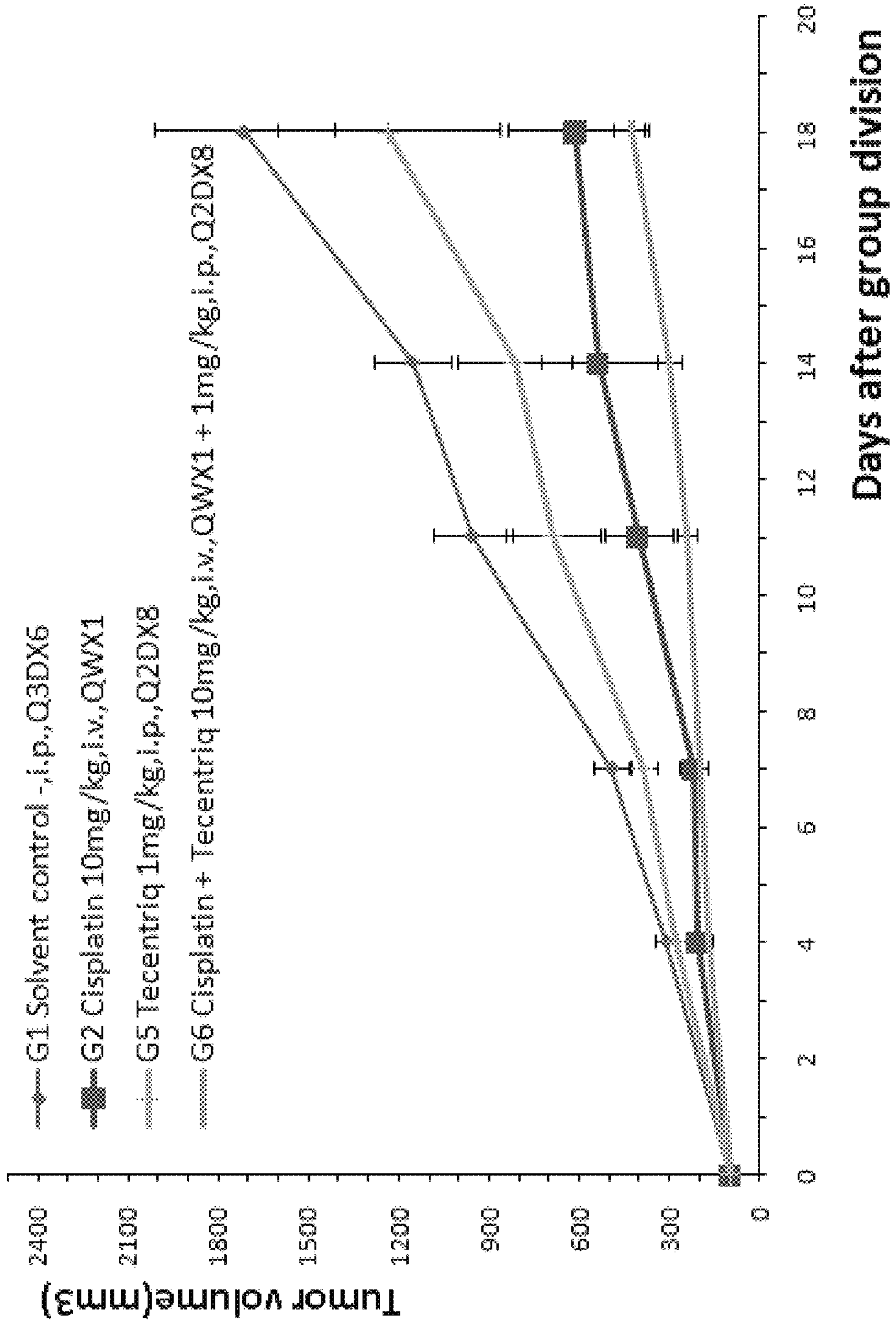
FIG. 20: the modified mouse colon cancer cells MC38-hPDL1 were transplanted into B-hPD-1 mice, and Cisplatin, Tecentriq, and their combination were used for anti-tumor efficacy tests; the average volume of tumors in experimental animals in the treatment groups was obviously smaller than that of the control group, and the volume of tumors in mice in the Cisplatin combined with Tecentriq group (G6) was significantly smaller than that of mice in the treatment group only using Cisplatin (G2) or the treatment group only using Tecentriq (G3), indicating that the therapeutic effect of combination was superior to the therapeutic effect of separate administration of Cisplatin or Keytruda.

From the testing results, it can be seen that there was no significant difference in weight change of mice in the 6 groups (FIG. 18) throughout the entire experiment period; from the tumor measurement results (FIGS. 19 and 20), however, tumors were growing continuously in the experiment period for the mice in the control group (G1). Compared with the control group, the volume of tumors in the 5 treatment groups (G2 to G6) decreased to different degrees, indicating that the tumor growth inside the mice was significantly inhibited after treatment by different drugs or after joint drug treatment.

Each experiment was specifically evaluated and analyzed. Main data and analytical results were listed in Table 10, specifically comprising tumor volumes at the time of group division (8 days after inoculation) and at 10 days after group division, tumor volumes when the experiments end (25 days after inoculation), situation of mice survival, situation of tumor-free mice, Tumor Growth Inhibition Value ($TGI_{TV}$), and statistical difference (P values) in mouse weights and tumor volumes between mice in the treatment groups and the control group. Among them, the survival situation was the worst for mice treated with Cisplatin only (G2), where 2 mice died, followed by the Cisplatin combined with Keytruda group (G4) or the Cisplatin combined with Tecentriq group (G6), each had one mouse died. On the other hand, all mice in the control group (G1) and the treatment groups using antibodies (G3 and G5) survive at the experiment end-point. At the experiment end-point, the average tumor volume of the control group (G1) was 1716±789 $mm^3$, the average tumor volume of the treatment group with Cisplatin only (G2) was 612±510 $mm^3$, the average tumor volume of the treatment group with Keytruda only (G3) was 1267±619 $mm^3$, the average tumor volume of the treatment group of Cisplatin combined with Keytruda (G4) was 496±160 $mm^3$, the average tumor volume of the treatment group with Tecentriq only (G5) was 1234±977 $mm^3$, and the average tumor volume of the treatment group of Cisplatin combined with Tecentriq (G6) was 427±148 $mm^3$. It can be seen that the tumor volume of the mice in the treatment group with combination of Cisplatin and Keytruda (G4) was significantly smaller than that of Cisplatin only (G2) or Keytruda only (G3); the tumor volume of the mice in the treatment group with combination of Cisplatin and Tecentriq (G6) was significantly smaller than that of Cisplatin only (G2) or Tecentriq only (G5). The experimental results show that the chemotherapy drug Cisplatin has certain tumor inhibitory effect, but has certain toxicity that can lead to mouse death. In addition, the $TGI_{TV}$ value also shows that the therapeutic effect of joint administration of the above two monoclonal antibodies and the chemotherapy drug Cisplatin was superior to the therapeutic effect of separate administration of the monoclonal antibodies or the chemotherapy drug. The simultaneous administration of the human PD-1 antibody Keytruda or the human PD-L1 antibody Tecentriq can more efficiently inhibit the growth of tumor cells.

TABLE 10

| | | Tumor volume ($mm^3$) | | | Survival | Tumor free | $TGI_{TV}$ | P values | |
|---|---|---|---|---|---|---|---|---|---|
| | | Day 8 | Day 18 | Day 25 | situation | situation | % | Weight | Tumor volume |
| Control group G1 | | 98 ± 23 | 954 ± 345 | 1716 ± 789 | 7/7(100%) | 0/7 | N/A | N/A | N/A |
| Treatment groups | G2 | 98 ± 24 | 401 ± 249 | 612 ± 510 | 5/7(71.4%) | 0/5 | 68.2 | 0.062 | 0.021 |
| | G3 | 98 ± 30 | 606 ± 247 | 1267 ± 619 | 7/7(100%) | 0/7 | 27.7 | 0.335 | 0.260 |
| | G4 | 97 ± 24 | 311 ± 117 | 496 ± 160 | 6/7(85.7%) | 0/6 | 75.3 | 0.136 | 0.004 |
| | G5 | 98 ± 26 | 688 ± 409 | 1234 ± 977 | 7/7(100%) | 0/7 | 29.8 | 0.598 | 0.330 |
| | G6 | 98 ± 30 | 242 ± 76 | 427 ± 148 | 6/7(85.7%) | 0/6 | 79.6 | 0.067 | 0.002 |

The above Examples have proven that the B-hPD-1 mouse model was respond to existing anti-human PD-1/PD-L1 inhibitors and chemotherapy drug or combination thereof, and has shown dosage correlation with tumor growth inhibition. The following Examples were selected anti-human PD-1/PD-L1 inhibitors to further prove that B-hPD-1 mice can be used as alternative living model for in vivo research and for screening, evaluating and treating of human PD-1/PD-L1 pathway regulators.

Example 12 Application of the B-hPD-1 Gene Humanized Animal Model in Screening Anti-Human PD-1/PD-L1 Regulators Experiment 1: B-hPD-1 homozygous mice (4-6 weeks old) were taken, $5\times10^5$ mouse colon cancer cells MC38-hPDL1 were subcutaneously inoculated at right side (the same as Example 10). When the tumor volume was about 100 $mm^3$, the mice were randomly divided into the control group or treatment groups (n=5/group). For the treatment group, the positive control Tecentriq or one of two anti-human PD-L1 antibodies was randomly selected, all dosages were 3 mg/kg, and a blank solvent was injected for the control group. The administration manner was intraperitoneal injection, once per 2 days for a total of 8 times. The tumor volume was measured twice a week. Moreover, euthanasia was performed when the tumor volume of a single mouse reached 3000 $mm^3$.

Main data and analytical results of all experiments were listed in Table 11, specifically comprising tumor volumes at the time of group division and at 10 days after group division, tumor volumes when the experiments end, situation of mice survival, situation of tumor-free mice, Tumor Growth Inhibition Value ($TGI_{TV}$), and statistical difference (P values) in mouse weights and tumor volumes between mice in the treatment groups and the control group.

TABLE 11

| | | Tumor volume ($mm^3$) | | | Survival | Tumor free | $TGI_{TV}$ | P values | |
|---|---|---|---|---|---|---|---|---|---|
| | | Day 10 | Day 20 | Day 27 | situation | situation | % | Weight | Tumor volume |
| Control group G1 | | 111 ± 27 | 247 ± 80 | 409 ± 131 | 5/5 | 0/5 | N/A | N/A | N/A |
| Treatment groups | G2(Tecentriq) | 111 ± 25 | 60 ± 70 | 75 ± 113 | 5/5 | 0/5 | 112.2 | 0.610 | 0.003 |
| | G3(PDL1-Ab1) | 111 ± 29 | 89 ± 54 | 101 ± 128 | 5/5 | 2/5 | 103.3 | 0.899 | 0.006 |
| | G4(PDL1-Ab2) | 112 ± 25 | 180 ± 71 | 232 ± 88 | 5/5 | 0/5 | 59.8 | 0.652 | 0.036 |

Figure 21:
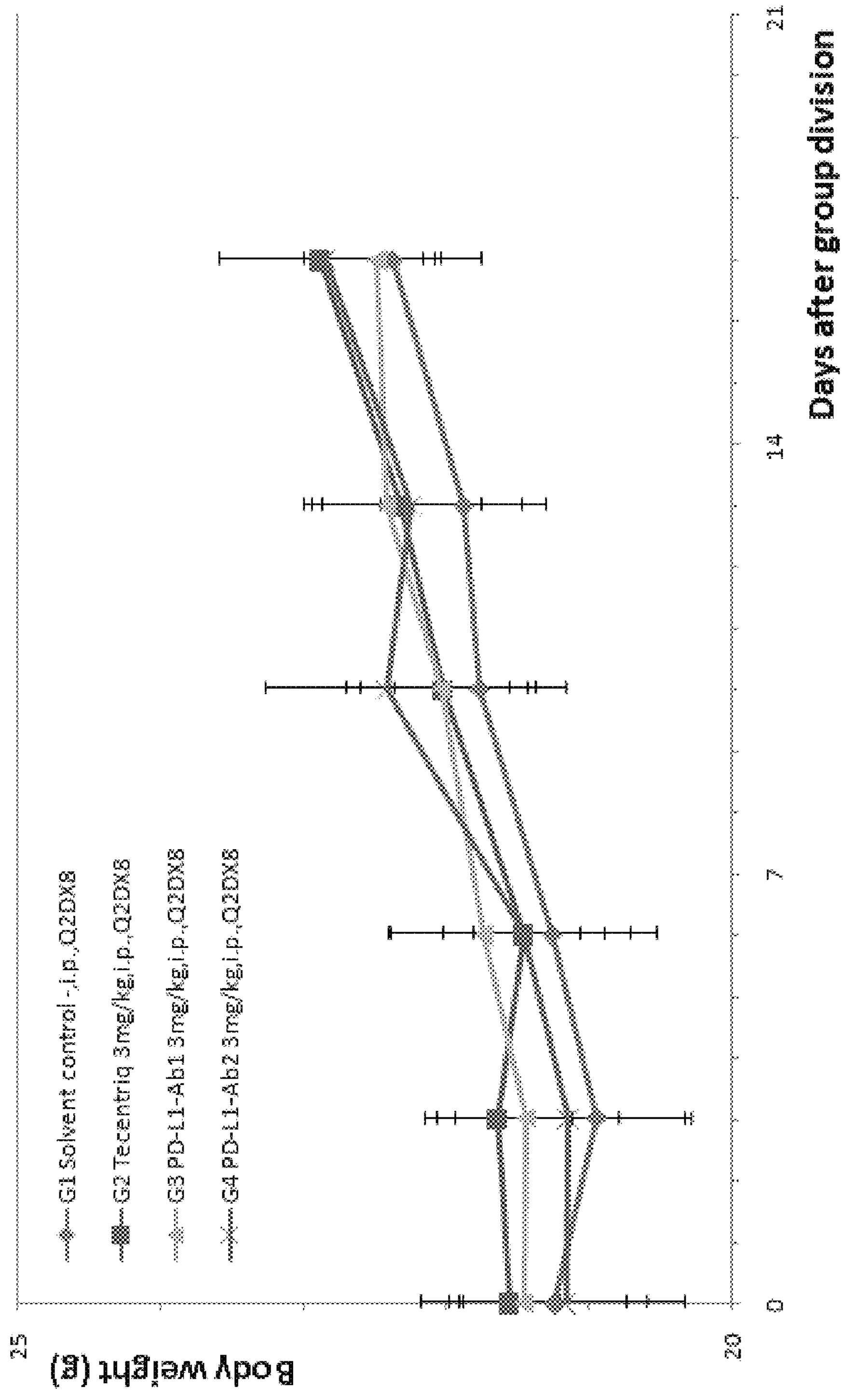
FIG. 21: the modified mouse colon cancer cells MC38-hPDL1 were transplanted into B-hPD-1 mice, the positive control Tecentriq or any one of anti-human PD-L1 antibodies PDL1-Ab1 and PDL1-Ab2 was used for anti-tumor efficacy tests, and there was no significant difference in average weight increase among experimental animals in the G1-G4 groups.
Figure 22:
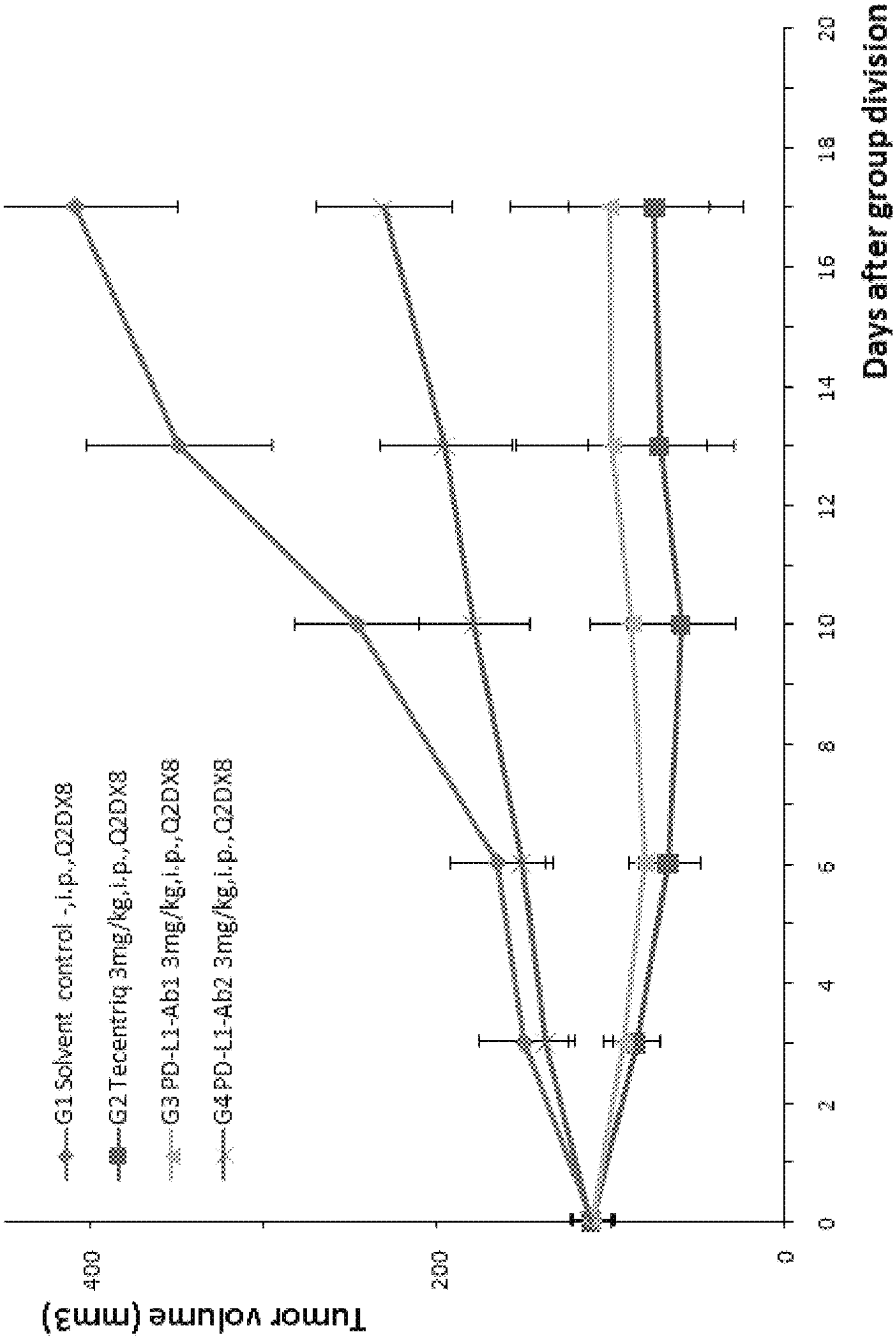
FIG. 22: the modified mouse colon cancer cells MC38-hPDL1 were transplanted into B-hPD-1 mice, the positive control Tecentriq or any one of anti-human PD-L1 antibodies PDL1-Ab1 and PDL1-Ab2 was used for anti-tumor efficacy tests, wherein there was no significant difference in the volume of tumors between mice in the treatment group using the PDL1-Ab1 antibody (G3) and the treatment group using Tecentriq (G2), and there was significant difference in the volume of tumors between G2 or G3 and the control group (G1) ($P<0.05$); on the other hand, the volume of tumors in mice treated with the PDL1-Ab2 antibody (G4) was significantly larger than that of the Tecentriq treatment group (G2) and the PDL1-Ab1 antibody treatment group (G3), indicating that under the same dosage and frequency, the anti-human PDL1-Ab1 antibody and the positive control Tecentriq have the similar therapeutic effect and have the similar effect on inhibiting tumor growth, while the anti-human PDL1-Ab2 antibody has a poorer therapeutic effect to that of Tecentriq or the PDL1-Ab1 antibody.

Overall, during the experiments of all groups, the animals were in good health. At each experiment end-point, the animals in all groups had normal weight gains. Compared with the control group, none of the treatment groups has a significant difference in animal weight (P>0.05), indicating that the animals have good tolerance against the three antibodies. There was no significant difference in weight among the mice in all the treatment groups and the control group (FIG. 21) throughout the entire experiment period. In terms of the tumor measurement results (FIG. 22), however, tumors were growing continuously in the experiment period for all mice in the control group. Compared with the control group, all the treatment groups have the volume of tumors shrunk to different degrees and/or disappears, indicating that the two anti-human PD-L1 monoclonal antibodies have different tumor inhibitory effects, do not have obvious toxicity on the animals, and have good safety.

At the experiment end-point, the average tumor volume of the control group (G1) was 409±131 $mm^3$, the average tumor volume of the Tecentriq treatment group (G2) was 75±113 $mm^3$, the average tumor volume of the PDL1-Ab1 antibody treatment group (G3) was 101±128 $mm^3$, and the average tumor volume of the PDL1-Ab2 antibody treatment group (G4) was 232±88 $mm^3$. The difference in tumor volume was not significant between mice in the PDL1-Ab1 antibody treatment group (G3) and the Tecentriq treatment group (G2), while there was a significant difference in tumor volume between G2, G3 and the control group (G1) ($P<0.05$), $TGI_{TV}$ was 112.2% and 103.3%, respectively. On the other hand, the tumor volume of the mice in the PDL1-Ab2 antibody treatment group (G4) was significantly bigger than that of the Tecentriq treatment group (G2) and the PDL1-Ab1 antibody treatment group (G3), indicating that the anti-human PDL1-Ab1 antibody has similar efficacy as that of the positive control Tecentriq under the same dosage and frequency, leading to equivalent effect on inhibiting tumor growth, while the efficacy of the anti-human PDL1-Ab2 antibody was not as good as that of Tecentriq or the PDL1-Ab1 antibody. This experiment proves that the B-hPD-1 mice can be used for screening drugs (e.g. antibodies) targeting human PD-L1 and for in vivo efficacy detection.

Experiment 2: B-hPD-1 homozygous mice (4-6 weeks old) were taken, mouse colon cancer cells MC38 ($5\times10^5$) were subcutaneously inoculated. When the tumor volume was about 100 $mm^3$, the mice were randomly divided into the control group or treatment groups (n=6/group). For the treatment group, one of five anti-human PD-1 antibodies was randomly selected, all dosages were 10 mg/kg, and a blank solvent was injected for the control group. The administration manner was intraperitoneal injection, once per 3 days for a total of 6 times. The tumor volume was measured twice a week. Moreover, euthanasia was performed when the tumor volume of a single mouse reached 3000 $mm^3$.

Main data and analytical results of all experiments were listed in Table 12, specifically comprising tumor volumes before group division and after group division, tumor volumes when the experiments end, situation of mice survival, situation of tumor-free mice, Tumor Growth Inhibition Value ($TGI_{TV}$), and statistical difference (P values) in mouse weights and tumor volumes between mice in the treatment groups and the control group.

TABLE 12

| | | Tumor volume ($mm^3$) | | | Survival | Tumor free | $TGI_{TV}$ | P values | |
|---|---|---|---|---|---|---|---|---|---|
| | | Day 6 | Day 18 | Day 26 | situation | situation | % | Weight | Tumor volume |
| Control group G1 | | 169 ± 16 | 1450 ± 202 | 3168 ± 606 | 5/5 | 0/5 | N/A | N/A | N/A |
| Treatment groups | G2(Ab-A) | 171 ± 20 | 330 ± 67 | 145 ± 58 | 5/5 | 2/5 | 101 | 0.13 | 0.0006 |
| | G3(Ab-B) | 168 ± 18 | 541 ± 235 | 744 ± 444 | 5/5 | 2/5 | 81 | 0.002 | 0.0091 |
| | G4(Ab-C) | 168 ± 26 | 309 ± 123 | 301 ± 200 | 5/5 | 1/5 | 95 | 0.03 | 0.0012 |
| | G5(Ab-D) | 167 ± 18 | 339 ± 69 | 97 ± 45 | 5/5 | 3/5 | 102 | 0.07 | 0.0005 |
| | G6(Ab-E) | 166 ± 18 | 448 ± 91 | 493 ± 184 | 5/5 | 0/5 | 89 | 0.04 | 0.0018 |

Figure 23:
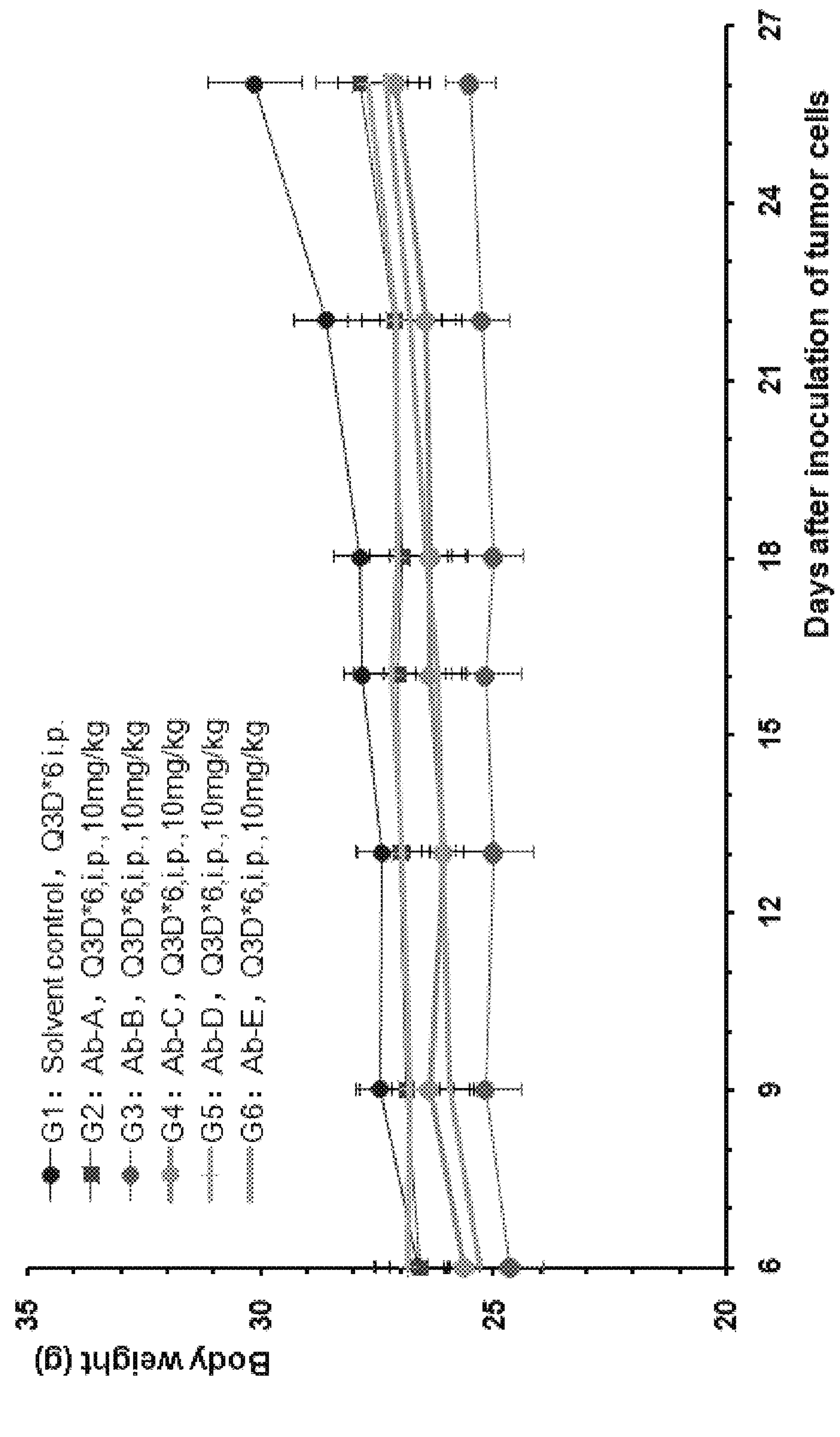
FIG. 23: the mouse colon cancer cells MC38 were transplanted into B-hPD-1 mice, five anti-human PD-1 antibodies were used for anti-tumor efficacy tests, and there was no significant difference in average weight increase among experimental animals in the G1-G6 groups.
Figure 24:
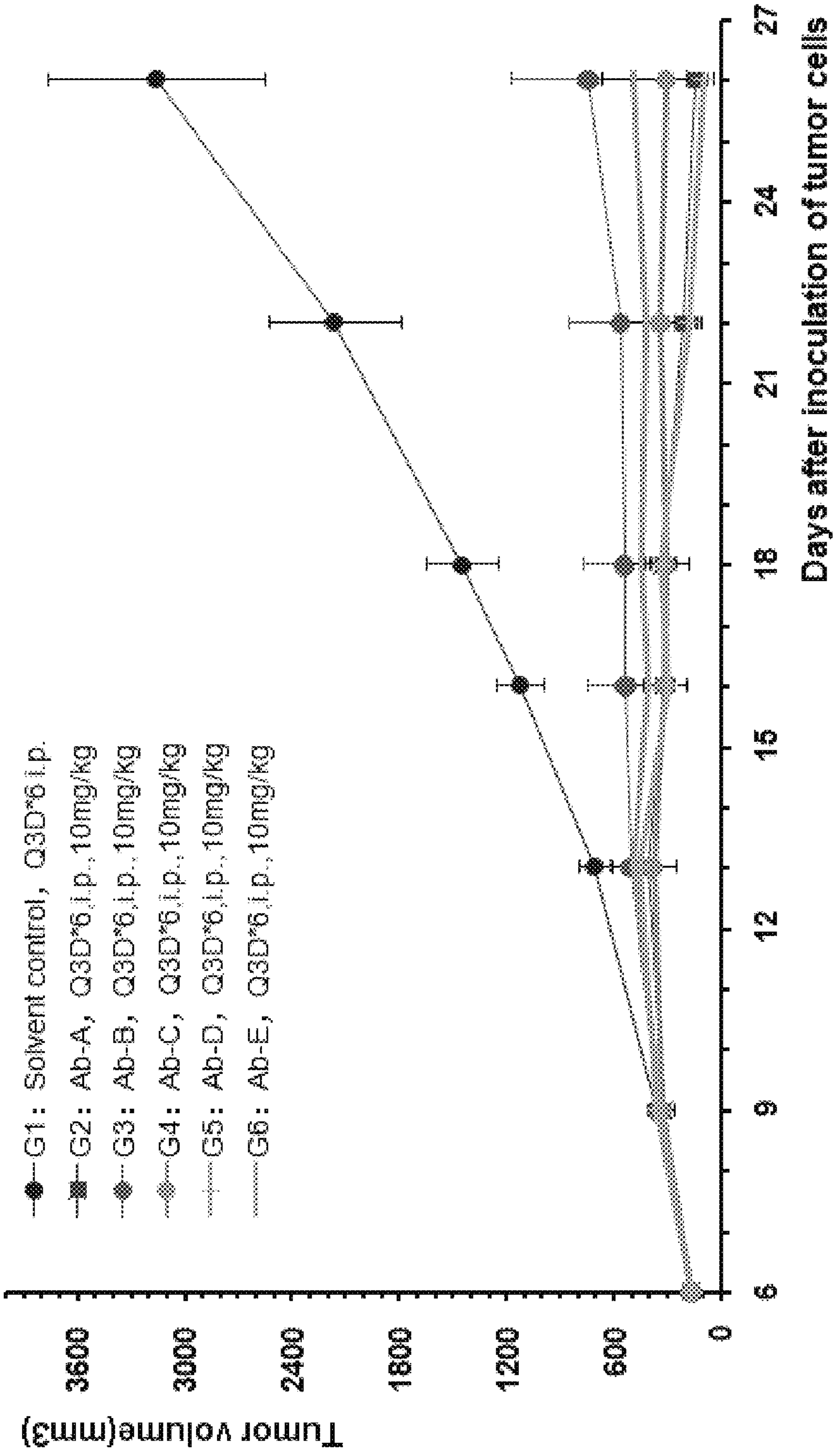
FIG. 24: the mouse colon cancer cells MC38 were transplanted into B-hPD-1 mice, five anti-human PD-1 antibodies were used for anti-tumor efficacy tests, and the volume of tumors in mice in all G2-G6 groups shrinks to different degrees and/or disappears compared with the control group, indicating that all five anti-human PD-1 monoclonal antibodies have excellent tumor inhibitory effect.

Overall, during the experiments of all groups, the animals were in good health. At each experiment end-point, the animals in all groups had normal weight gains. Compared with the control group, none of the treatment groups has a significant difference in animal weight, indicating that the animals have good tolerance against the five antibodies. There was no significant difference in weight among the mice in all the treatment groups and the control group (FIG. 23) throughout the entire experiment period. In terms of the tumor measurement results (FIG. 24), however, tumors were growing continuously in the experiment period for all mice in the control group. Compared with the control group, all the treatment groups have the volume of tumors shrunk to different degrees and/or disappears, indicating that the five anti-human PD-1 monoclonal antibodies have different tumor inhibitory effects, do not have obvious toxicity on the animals, and have good safety. This experiment proves that the B-hPD-1 mice can be used for screening drugs (e.g. antibodies) targeting human PD-1 and for in vivo efficacy detection.

Example 13 Preparation and Identification of Double Humanized or Multiple Humanized Mice The B-hPD-1 mice using this method or already prepared can be further used to prepare a double-gene humanized or multi-gene humanized mouse model. For example, in Example 8 above, the fertilized egg used in the microinjection and embryo transfer were fertilized egg from other gene modified mice. The fertilized egg of the B-hPD-1 mice can be selected for gene editing to further obtain a PD-1 gene humanized and other gene modified double-gene or multi-gene modified or humanized mouse model. Alternatively, the B-hPD-1 homozygous mice or heterozygous mice obtained using this method can copulate with other gene modified homozygous or heterozygous mice, the progenies thereof were screened, and according to the Mendel's genetic law, there was a probability that a PD-1 gene humanized and other gene modified double-gene or multi-gene modified or humanized mouse model can be obtained. Then, the heterozygous mice were subjected to mutual copulation to obtain double-gene or multi-gene modified or humanized heterozygous mice.

The preparation of double humanized CTLA-4/PD-1 mice was used as an example. Since mouse CTLA-4 gene and PD-1 gene were on the same chromosome (#1 chromosome), the fertilized egg of B-hCTLA-4 (CTLA-4 gene humanized) mice were selected for gene editing during the microinjection in Example 8, and the CTLA-4/PD-1 gene double humanized mice were ultimately obtained through screening positive mouse progenies.

Figure 25:
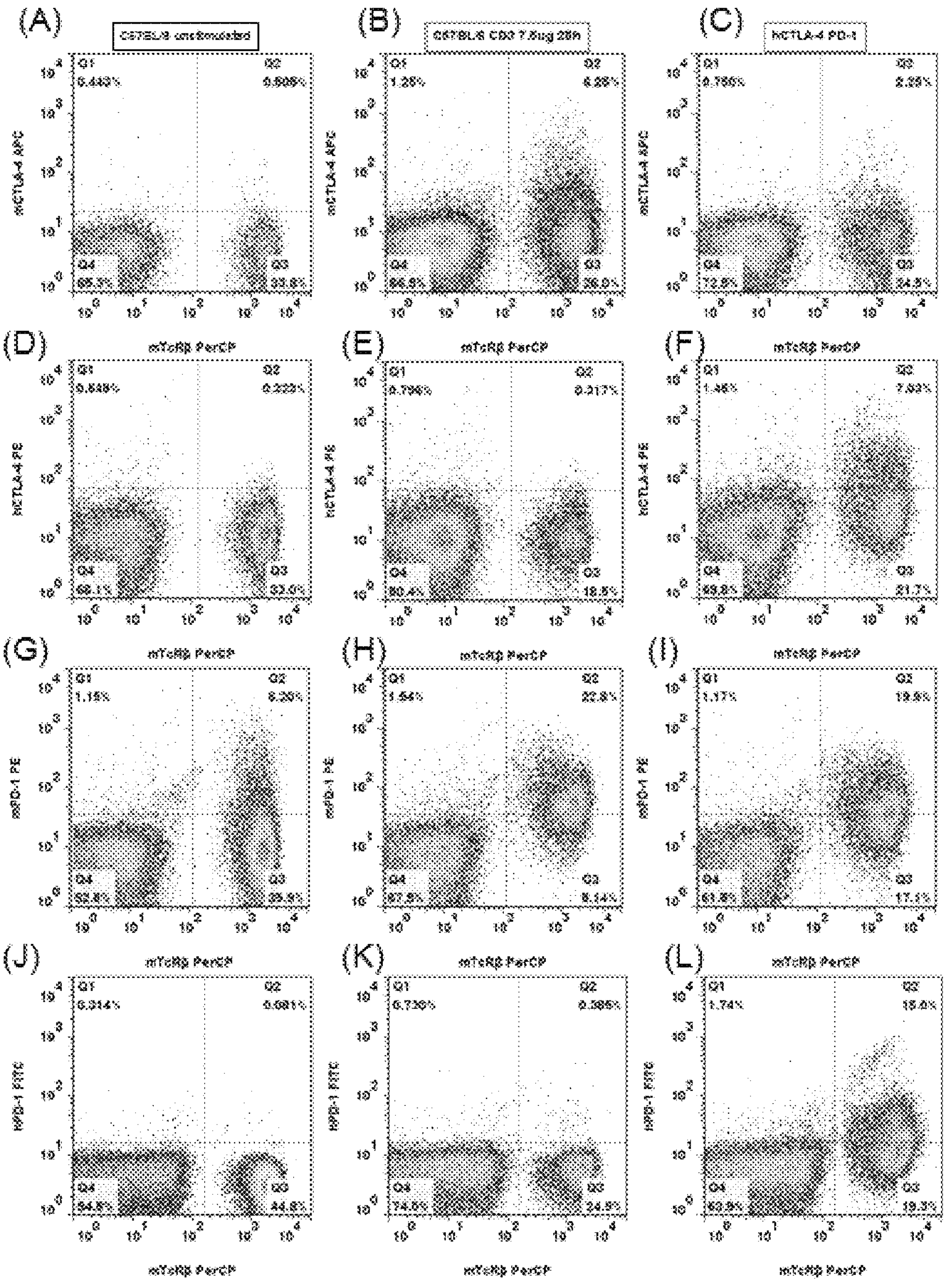
FIG. 25: flow cytometry results, wherein C57BL/6 mice and double humanized CTLA-4/PD-1 heterozygous mice were taken, their T-cells in spleens were activated through the anti-mouse CD3 antibody, respectively, then the anti-mouse CTLA-4 antibody mCTLA-4 APC (FIGs. A, B, C) or the human-source CTLA-4 antibody hCTLA-4 PE (FIGs. D, E, F), or the anti-mouse PD-1 antibody mPD-1 PE (FIGs. G, H, I) or the anti-human PD-1 antibody hPD-1 FITC (FIGs. J, K, L), and the anti-mouse T-cell surface antibody mTcRrβ were used simultaneously for cell labeling T-cell extracellular proteins; cells that express the human CTLA-4 and PD-1 proteins were detected in the spleens of the gene double humanized CTLA-4/PD-1 heterozygous mice, while no cells that express the human CTLA-4 or PD-1 protein were detected in the spleens of the C57BL/6 control mice.

One double humanized CTLA-4/PD-1 heterozygote (6-weeks old) was selected, two wild-type C57BL/6 mice were selected as the control, 7.5 μg mouse CD3 antibody was administered to the mice through intraperitoneal injection, and after 28 h, the mice were subjected to euthanasia through neck break. Their spleens were taken, ground and filtered through a 70 μm cell screen. The filtered cell suspension was centrifuged, the supernatant was discarded, an erythrocyte lysate was added, after 5 min of lysis, and a PBS solution was added to neutralize the lysis reaction. The solution was centrifuged, the supernatant was discarded, and the cells were washed with PBS once, then the anti-mouse CTLA-4 antibody mCTLA-4 APC (FIGS. 25A, 25B, 25C) or the anti-human CTLA-4 antibody hCTLA-4 PE (FIGS. 25D, 25E, 25F), or the anti-mouse PD-1 antibody mPD-1 PE (FIGS. 25G, 25H, 25I) or the anti-human PD-1 antibody hPD-1 FITC (FIGS. 25J, 25K, 25L), and the anti-mouse T-cell surface antibody mTcRβ were used for staining the isolated T-cell extracellular proteins, and after the cells were washed with PBS, flow cytometry was performed to detect protection expression. The flow cytometry results were shown in FIG. 25. Compared with the C57BL/6 mice unstimulated and with T-cells in spleens activated through stimulation by the mouse CD3 antibody, T cells that express the human CTLA-4 and PD-1 proteins can be detected in the spleens of the gene humanized CTLA-4/PD-1 heterozygous mice for both the human-source CTLA-4 antibody and the human-source PD-1 antibody, while no T cells that express the human CTLA-4 or PD-1 protein were detected in the spleens of the C57BL/6 control mice.

INDUSTRIAL APPLICABILITY

The present invention provides a method for preparing a PD-1 gene-modified humanized animal model. The model utilizes the CRIPSR/Cas9 technique to replace partial fragments of a mouse PD-1 gene with fragments of a human PD-1 gene in a manner of DNA homologous recombination by constructing a targeting vector, thereby preparing a PD-1 gene-modified humanized mouse. This mouse can normally express a PD-1 protein containing the functional domain of the human PD-1 protein, and can be used as an animal model for signal mechanism research regarding PD-1, PD-L1 and other genes and proteins, for screening individual or multiple effective regulators and drugs, and for pharmacological research. The method has an important application value in studies on functions of the PD-1 and PD-L1 genes and in the development of new drugs.

The invention claimed is:

1. A genetically modified mouse whose genome comprises a nucleic acid sequence encoding a chimeric programmed cell death 1 (PD-1) protein comprising the amino acid sequence of SEQ ID NO: 17 operably, linked to a promoter of the mouse PD-1 gene, and wherein the mouse functionally expresses the chimeric PD-1.

2. The genetically modified mouse of claim 1, wherein the mouse has a C57BL/6 background.

3. The genetically modified mouse of claim 1, wherein the genome of the mouse comprises a nucleic acid sequence that has at least 80% homology to the nucleic acid sequence of SEQ ID NO: 21 operably linked to the promoter of the mouse PD-1 gene.

4. A cell or tissue isolated from the genetically modified mouse of claim 1.

5. The genetically modified mouse of claim 1, wherein the genome of the mouse comprises the nucleic acid sequence of SEQ ID NO: 21 operably linked to the promoter of the mouse PD-1 gene.

6. The genetically modified mouse of claim 1, wherein the genome of the mouse further comprises a nucleic acid sequence encoding a humanized CTLA-4.

7. A method of preparing a genetically modified mouse, the method comprising:

1) providing a plasmid comprising a human PD-1 gene fragment that comprises a nucleic acid sequence that has at least 80% homology to the nucleic acid sequence of SEQ ID NO: 21 flanked by a 5' homology arm and a 3' homology arm, wherein the 5' and 3' homology arms target exon 2 of a mouse PD-1 gene;

2) providing two small guide RNAs (sgRNAs) that target the nucleic add sequences of SEQ ID NO: 1-4 and SEQ ID NO: 5-8;

3) modifying the genome of a mouse embryo using the plasmid of step 1), the sgRNAs of step 2) and Cas9; and 4) transplanting the embryo obtained in step 3) into a recipient mouse such a transgenic mouse is obtained, wherein the transgenic mouse has a genome comprising a nucleic acid sequence encoding a chimeric programmed cell death 1 (PD-1) protein comprising the an acid sequence of SEQ ID NO: 17 operably linked to a promoter of the mouse PD-1 gene, and wherein the mouse functionally expresses the chimeric PD-1.

8. The method of claim 7, wherein the 5' homology arm has the nucleic acid sequence of SEQ ID NO: 18, and the 3' homology arm has the nucleic acid sequence of SEQ ID NO: 24.

9. A method of evaluating a drug for the treatment of cancer, the method comprising:

a) administering a drug to a genetically modified mouse that has a tumor, and b) determining whether the drug inhibits the tumor, wherein the genetically modified mouse has a genome comprising a nucleic acid sequence encoding a chimeric programmed cell death 1 (PD-1) protein comprising the amino add sequence of SEQ ID NO: 17 operably linked to a promoter of the mouse PD-1 gene, and wherein the mouse functionally expresses the chimeric PD-1.

10. The method of claim 9, wherein the tumor expresses human PD-L1.

11. The method of claim 9, wherein the genome of the mouse further comprises a nucleic acid sequence encoding a humanized CTLA-4.

12. The method of claim 9, wherein the drug is an anti-human PD-1 antibody.

13. The method of claim 9, wherein the sgRNAs target the nucleic acid sequences of SEQ ID NO: 3 and SEQ ID NO: 8.

* * * * *

SEQUENCE LISTING

<160> NUMBER OF SEQ ID NOS: 38

<210> SEQ ID NO 1
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 1
agggacctcc agggcccatt ggg 23

<210> SEQ ID NO 2
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 2
cagaggtccc caatgggccc tgg 23

<210> SEQ ID NO 3
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 3
gtagaaggtg agggacctcc agg 23

<210> SEQ ID NO 4
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 4
ccctcacctt ctacccagcc tgg 23

<210> SEQ ID NO 5
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 5
gcaccccaag gcaaaaatcg agg 23

-continued

<210> SEQ ID NO 6
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 6
ggagcagagc tcgtggtaac agg 23

<210> SEQ ID NO 7
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 7
gttaccacga gctctgctcc agg 23

<210> SEQ ID NO 8
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 8
gcaaaaatcg aggagagccc tgg 23

<210> SEQ ID NO 9
<211> LENGTH: 19
<212> TYPE: DNA
<213> ORGANISM: Artificial Sequence
<220> FEATURE:
<223> OTHER INFORMATION: sgRNA sequence

<400> SEQUENCE: 9
tagaaggtga gggacctcc 19

<210> SEQ ID NO 10
<211> LENGTH: 19
<212> TYPE: DNA
<213> ORGANISM: Artificial Sequence
<220> FEATURE:
<223> OTHER INFORMATION: sgRNA sequence

<400> SEQUENCE: 10
ggaggtccct caccttcta 19

<210> SEQ ID NO 11
<211> LENGTH: 19
<212> TYPE: DNA
<213> ORGANISM: Artificial Sequence
<220> FEATURE:
<223> OTHER INFORMATION: sgRNA sequence

<400> SEQUENCE: 11
caaaaatcga ggagagccc 19

<210> SEQ ID NO 12
<211> LENGTH: 19
<212> TYPE: DNA
<213> ORGANISM: Artificial Sequence
<220> FEATURE:
<223> OTHER INFORMATION: sgRNA sequence

<400> SEQUENCE: 12
gggctctcct cgatttttg 19

<210> SEQ ID NO 13
<211> LENGTH: 132
<212> TYPE: DNA
<213> ORGANISM: Artificial Sequence
<220> FEATURE:
<223> OTHER INFORMATION: Synthesized sequence

<400> SEQUENCE: 13
gaattctaat acgactcact atagggggtc ttcgagaaga cctgttttag agctagaaat 60
agcaagttaa aataaggcta gtccgttatc aacttgaaaa agtggcaccg agtcggtgct 120
tttaaaggat cc 132

<210> SEQ ID NO 14
<211> LENGTH: 679
<212> TYPE: DNA
<213> ORGANISM: Artificial Sequence
<220> FEATURE:
<223> OTHER INFORMATION: Human and mouse

<400> SEQUENCE: 14
atgctgaagg aagagccctg cttgttggag gttacttatt cacaacctac aagaagctac 60
aagctcctag gtagggggaa ctgcttacga tattctgccc tggaatgggt ctgagagcac 120
attcctctcc aggggttca gaaaagatgt cagaaagggt gtacaggctc cttcctcaca 180
gctctttgtt cttctgcatt tcagaggtcc ccaatgggcc ctggaacccc cccaccttct 240
ccccagccct gctcgtggtg accgaagggg acaacgccac cttcacctgc agcttctcca 300
acacatcgga gagcttcgtg ctaaactggt accgcatgag ccccagcaac cagacggaca 360
agctggccgc cttccccgag gaccgcagcc agcccggcca ggactgccgc ttccgtgtca 420
cacaactgcc caacgggcgt gacttccaca tgagcgtggt cagggcccgg cgcaatgaca 480
gcggcaccta cctctgtggg gccatctccc tggcccccaa ggcgcagatc aaagagagcc 540
tgcgggcaga gctcgtggta acaggtgagg ctagtagaac ctacgtgggc aattccttcc 600
tgcccagaga cctcttaggc tctctgccat ggctctgcct agagccttga cgacactgcc 660
cctctccctg tggaaatcc 679

<210> SEQ ID NO 15
<211> LENGTH: 867
<212> TYPE: DNA
<213> ORGANISM: Artificial Sequence
<220> FEATURE:
<223> OTHER INFORMATION: Human and mouse

<400> SEQUENCE: 15
atgtgggtcc ggcaggtacc ctggtcattc acttgggctg tgctgcagtt gagctggcaa 60
tcagggtggc ttctagaggt ccccaatggg ccctggaacc cccccacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggcc 240
gccttccccg aggaccgcag ccagcccggc caggactgcc gcttccgtgt cacacaactg 300
cccaacgggc gtgacttcca catgagcgtg gtcagggccc ggcgcaatga cagcggcacc 360
tacctctgtg gggccatctc cctggccccc aaggcgcaga tcaaagagag cctgcgggca 420

-continued

```
gagctcgtgg taacagagag aatcctggag acctcaacaa gatatcccag cccctcgccc    480

aaaccagaag gccggtttca aggcatggtc attggtatca tgagtgccct agtgggtatc    540

cctgtattgc tgctgctggc ctgggcccta gctgtcttct gctcaacaag tatgtcagag    600

gccagaggag ctggaagcaa ggacgacact ctgaaggagg agccttcagc agcacctgtc    660

cctagtgtgg cctatgagga gctggacttc cagggacgag agaagacacc agagctccct    720

accgcctgtg tgcacacaga atatgccacc attgtcttca ctgaagggct gggtgcctcg    780

gccatgggac gtaggggctc agctgatggc ctgcagggtc ctcggcctcc aagacatgag    840

gatggacatt gttcttggcc tctttga                                        867
```

<210> SEQ ID NO 16
<211> LENGTH: 1972
<212> TYPE: DNA
<213> ORGANISM: Artificial Sequence
<220> FEATURE:
<223> OTHER INFORMATION: Human and mouse

<400> SEQUENCE: 16

```
tgagcagcgg ggaggaggaa gaggagactg ctactgaagg cgacactgcc aggggctctg     60

ggcatgtggg tccggcaggt accctggtca ttcacttggg ctgtgctgca gttgagctgg    120

caatcagggt ggcttctaga ggtccccaat gggccctgga acccccccac cttctcccca    180

gccctgctcg tggtgaccga aggggacaac gccaccttca cctgcagctt ctccaacaca    240

tcggagagct tcgtgctaaa ctggtaccgc atgagcccca gcaaccagac ggacaagctg    300

gccgccttcc ccgaggaccg cagccagccc ggccaggact gccgcttccg tgtcacacaa    360

ctgcccaacg ggcgtgactt ccacatgagc gtggtcaggg cccggcgcaa tgacagcggc    420

acctacctct gtggggccat ctccctggcc cccaaggcgc agatcaaaga gagcctgcgg    480

gcagagctcg tggtaacaga gagaatcctg gagacctcaa caagatatcc cagcccctcg    540

cccaaaccag aaggccggtt tcaaggcatg gtcattggta tcatgagtgc cctagtgggt    600

atccctgtat tgctgctgct ggcctgggcc ctagctgtct tctgctcaac aagtatgtca    660

gaggccagag gagctggaag caaggacgac actctgaagg aggagccttc agcagcacct    720

gtccctagtg tggcctatga ggagctggac ttccagggac gagagaagac accagagctc    780

cctaccgcct gtgtgcacac agaatatgcc accattgtct tcactgaagg gctgggtgcc    840

tcggccatgg gacgtagggg ctcagctgat ggcctgcagg gtcctcggcc tccaagacat    900

gaggatggac attgttcttg gcctctttga ccagattctt cagccattag catgctgcag    960

accctccaca gagagcaccg gtccgtccct cagtcaagag gagcatgcag gctacagttc   1020

agccaaggct cccagggtct gagctagctg gagtgacagc ccagcgcctg caccaattcc   1080

agcacatgca ctgttgagtg agagctcact tcaggtttac cacaagctgg gagcagcagg   1140

cttcccggtt tcctattgtc acaaggtgca gagctggggc ctaagcctat gtctcctgaa   1200

tcctactgtt gggcacttct agggacttga gacactatag ccaatggcct ctgtgggttc   1260

tgtgcctgga aatggagaga tctgagtaca gcctgctttg aatggccctg tgaggcaacc   1320

ccaaagcaag gggtccagg tatactatgg gcccagcacc taaagccacc cttgggagat    1380

gatactcagg tgggaaattc gtagactggg ggactgaacc aatcccaaga tctggaaaag   1440

ttttgatgaa gacttgaaaa gctcctagct tcgggggtct gggaagcatg agcacttacc   1500

aggcaaaagc tccgtgagcg tatctgctgt ccttctgcat gcccaggtac ctcagttttt   1560

ttcaacagca aggaaactag ggcaataaag ggaaccagca gagctagagc cacccacaca   1620
```

```
tccagggggc acttgactct ccctactcct cctaggaacc aaaaggacaa agtccatgtt   1680

gacagcaggg aaggaaaggg ggatataacc ttgacgcaaa ccaacactgg ggtgttagaa   1740

tctcctcatt cactctgtcc tggagttggg ttctggctct ccttcacacc taggactctg   1800

aaatgagcaa gcacttcaga cagtcagggt agcaagagtc tagctgtctg gtgggcaccc   1860

aaaatgacca gggcttaagt ccctttcctt tggtttaagc ccgttataat taaatggtac   1920

caaaagcttt aaaaaaaaaa aaaaaaaaaa aaaaaaaaaa aaaaaaaaaa aa           1972


<210> SEQ ID NO 17
<211> LENGTH: 288
<212> TYPE: PRT
<213> ORGANISM: Artificial Sequence
<220> FEATURE:
<223> OTHER INFORMATION: Human and mouse

<400> SEQUENCE: 17

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285


<210> SEQ ID NO 18
```

-continued

<211> LENGTH: 1770
<212> TYPE: DNA
<213> ORGANISM: Artificial Sequence
<220> FEATURE:
<223> OTHER INFORMATION: mouse

<400> SEQUENCE: 18

```
tggcccatag agaccaatgt ggaccactgc tcaccctgcc cagaaccata tgacccagtc     60
ttcaccaact ctgcatggaa tctagggatc ctggcccttg aggagcgcca gacccagctc    120
ataggccacg cccaccctca ggtctaagtg acattagatt atctgtatgt tcatcatcca    180
tggtacagct gagaacatca aggagggaaa gtggcagtcc tacttttcgc catgtggtga    240
tggagaccat ttctgggcaa ggctacatgg tgcggatgga tgtctctggg tttgcctctg    300
ctgaagtctg cttgctcact gcagacagct ctgccacgta tctctggctt cctttctgcg    360
ctggaagatt tcacatacct tgtttgccag gtgttttggg cctcagttct ccccccatcc    420
agcttctccc taactggccc ctcttctttg cctctgaccc ctgctttctg agcccataac    480
cttagctgtg gcagcacagc ctctctcttt gtacccctgg gagggaacca tgcccggtta    540
gtattgtcaa ataccccaca tcagaggcgg gtgtgaggtt tggggtgcag tgccctgggc    600
catgtaatcg ggtagaattc cctccctata tgactactca atccgtggga ggagagggca    660
gagggctgga aaggatgcag ctggggacat gtctattcgc actggcgctt tctctacgag    720
ccccagttgc caaatgacta catcggctaa agagagctgg cagcccagac agagttgagg    780
ccagagcagc ttcaaagatg tcttggtgcc tgtttcctgt gtgcatgtca gtctcctctg    840
ggtaaggccc acatgtgtgt gctcagcaag tctgtatttc cttgaccctg agccttctga    900
ccgtacctac atacccaacc gcacctatat acccgaccgc aggttcaact gctgacatca    960
tatgggtccc agtagtgggt acttttgagt gctggtggaa tgttatgtgt tatgtgtcag   1020
tgtgcattta tgtggcaaga agcttgccag tgcggcaggc atttcctgag aagagccatg   1080
agaccctgca tgctgcctga ccctggcagt accacccaga acactttatt tgggtgagcc   1140
tagaccttct gtccacttga gagacaatga cacagctgat ctttggaggc ttcttgctgt   1200
gacctctgat ctggctggaa gacatgactg ctaccctatg ccttctgcta ctcagggtag   1260
ctctgacatg cttggtgggc tccctgggac aaaatactgc ctggacccca agcttactaa   1320
agaatccacc ctctccaagt ctgaggtttc catggaaacc ctacactccc acctcactat   1380
cccactgacc cttcagacag aactaggcta gccaaccaga agtctaagac tggaacattc   1440
aggtcaggcc tggaacatct tgaacaggag tgggaaggta gagacatctt cggggaaaat   1500
atcccaaagt ctcaaaggac agaatagtag cctccagacc ctaggttcag ttatgctgaa   1560
ggaagagccc tgcttgttgg aggttactta ttcacaacct acaagaagct acaagctcct   1620
aggtaggggg aactgcttac gatattctgc cctggaatgg gtctgagagc acattcctct   1680
ccagggggtt cagaaaagat gtcagaaagg gtgtacaggc tccttcctca cagctctttg   1740
ttcttctgca tttcagaggt ccccaatggg                                     1770
```

<210> SEQ ID NO 19
<211> LENGTH: 49
<212> TYPE: DNA
<213> ORGANISM: Artificial Sequence
<220> FEATURE:
<223> OTHER INFORMATION: PCR primer

<400> SEQUENCE: 19

```
tacctttaag aaggagatat acatgtggcc catagagacc aatgtggac                 49
```

<210> SEQ ID NO 20
<211> LENGTH: 22
<212> TYPE: DNA
<213> ORGANISM: Artificial Sequence
<220> FEATURE:
<223> OTHER INFORMATION: PCR primer

<400> SEQUENCE: 20
ggttccaggg cccattgggg ac 22

<210> SEQ ID NO 21
<211> LENGTH: 333
<212> TYPE: DNA
<213> ORGANISM: Artificial Sequence
<220> FEATURE:
<223> OTHER INFORMATION: human

<400> SEQUENCE: 21
ccctggaacc cccccacctt ctccccagcc ctgctcgtgg tgaccgaagg ggacaacgcc 60
accttcacct gcagcttctc caacacatcg gagagcttcg tgctaaactg gtaccgcatg 120
agccccagca accagacgga caagctggcc gccttccccg aggaccgcag ccagcccggc 180
caggactgcc gcttccgtgt cacacaactg cccaacgggc gtgacttcca catgagcgtg 240
gtcagggccc ggcgcaatga cagcggcacc tacctctgtg gggccatctc cctggccccc 300
aaggcgcaga tcaaagagag cctgcgggca gag 333

<210> SEQ ID NO 22
<211> LENGTH: 22
<212> TYPE: DNA
<213> ORGANISM: Artificial Sequence
<220> FEATURE:
<223> OTHER INFORMATION: PCR primer

<400> SEQUENCE: 22
ccccaatggg ccctggaacc cc 22

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
ttaccacgag ctctgcccgc ag 22

<210> SEQ ID NO 24
<211> LENGTH: 1733
<212> TYPE: DNA
<213> ORGANISM: Artificial Sequence
<220> FEATURE:
<223> OTHER INFORMATION: mouse

<400> SEQUENCE: 24
ctcgtggtaa caggtgaggc tagtagaacc tacgtgggca attccttcct gcccagagac 60
ctcttaggct ctctgccatg gctctgccta gagccttgac gacactgccc ctctccctgt 120
ggaaatcctc agatgcccat ttacctttaa gggatggaag ggcttgccaa agtagggtgg 180
gtggccagtc actgcccatc taaaatagtc ccttgggact tggtgaggac agggtgtgtg 240
accctaaaga aaatacacta tcggtgtcct agaactctat tctttgtcat cctgtagaga 300

-continued

```
gaatcctgga gacctcaaca agatatccca gcccctcgcc caaaccagaa ggccggtttc    360

aaggcatggt cattggtatc atgagtgccc tagtgggtat ccctgtattg ctgctgctgg    420

cctgggccct agctgtcttc tgctcaacaa gtatgtcagg taaggctcat cataccctgc    480

ttctgtcctg ccaaaccttg tagtcactgt acttcacaca tacgtagatc accagaaggg    540

tggtcatgca ccacacacac tctgaccact acaaaagcct gtggccgccc cacccacacc    600

tagcctcagg ctgctggctt tcctaaacaa ctagtgagag ctgccacctc caggaggtct    660

ggtcatcagc cagctaagag gccacagcta atatctgcta catgcctacc ctgtgttgtg    720

gtacaccagg aaaggggaca ctgatgcacc tgtgcctgtg gcaggcccta ctcctcaatt    780

cattgtccta ccaggaactc cccgttagta aatgggaagg gtgcccgtgg ggatggaaag    840

gctggtgctt gcccatggtg tagatctctt cagtgcctga cacgcccctc ctgagcacac    900

aaaacacaca cacacacaca cacacacaca cacacacaca cacacacgag agagaaagat    960

ggagagacag agggaggaca ttcctccact agggaagatg gctctgtagc tgccctctaa   1020

cccaaactgt gtgtctcaac agaggccaga ggagctggaa gcaaggacga cactctggtg   1080

agtatgagtt ttctttcttg agtgatctat cccaggccac ccccaggtct tggtacaggt   1140

agagagacca tggggcctac agggctagag cctggagagc ccagctccca ttttctacca   1200

ggcccccaga gccatatcct gttgttcctc ccagcagctg accccactgt gtgtacccct   1260

gtcgtgtcca acgtggtcac gacttgtttt cttctgtgca gagacaaggg gcaaaagtca   1320

aattttggaa tcctaaaccc gccaggaaac atttaacgat agaaactggg ccagaaacac   1380

gaggctgcac cctaaatatc aagaagtcaa tggggagcct atggcctctg tgggttctgt   1440

gcctgggcag ctgttaggtc aggtcccagc ttccatgact gaggtgaatt tgctctaaga   1500

agaaccccaa atccagtgtc agtctggaaa cccagcatag ggaagggttg agattatggg   1560

atgcacacac caccccccaa ctgactataa caatggctct ttcttctccc ccctcccctg   1620

ccccttgaag aaggaggagc cttcagcagc acctgtccct agtgtggcct atgaggagct   1680

ggacttccag ggacgagaga agacaccaga gctccctacc gcctgtgtgc aca           1733
```

```
<210> SEQ ID NO 25
<211> LENGTH: 24
<212> TYPE: DNA
<213> ORGANISM: Artificial Sequence
<220> FEATURE:
<223> OTHER INFORMATION: PCR primer

<400> SEQUENCE: 25

gcgggcagag ctcgtggtaa cagg                                             24


<210> SEQ ID NO 26
<211> LENGTH: 35
<212> TYPE: DNA
<213> ORGANISM: Artificial Sequence
<220> FEATURE:
<223> OTHER INFORMATION: PCR primer

<400> SEQUENCE: 26

tgttagcagc cggatctcag tgtgcacaca ggcgg                                 35


<210> SEQ ID NO 27
<211> LENGTH: 26
<212> TYPE: DNA
<213> ORGANISM: Artificial Sequence
<220> FEATURE:
<223> OTHER INFORMATION: PCR primer
```

<400> SEQUENCE: 27
agacatcata ctggcaaccc ctagcc 26

<210> SEQ ID NO 28
<211> LENGTH: 25
<212> TYPE: DNA
<213> ORGANISM: Artificial Sequence
<220> FEATURE:
<223> OTHER INFORMATION: PCR primer

<400> SEQUENCE: 28
gcggtaccag tttagcacga agctc 25

<210> SEQ ID NO 29
<211> LENGTH: 24
<212> TYPE: DNA
<213> ORGANISM: Artificial Sequence
<220> FEATURE:
<223> OTHER INFORMATION: PCR primer

<400> SEQUENCE: 29
tcgtggtgac cgaaggggac aacg 24

<210> SEQ ID NO 30
<211> LENGTH: 25
<212> TYPE: DNA
<213> ORGANISM: Artificial Sequence
<220> FEATURE:
<223> OTHER INFORMATION: PCR primer

<400> SEQUENCE: 30
agcctgcatg ctcctcttga ctgag 25

<210> SEQ ID NO 31
<211> LENGTH: 24
<212> TYPE: DNA
<213> ORGANISM: Artificial Sequence
<220> FEATURE:
<223> OTHER INFORMATION: PCR primer

<400> SEQUENCE: 31
ccagcacatg cactgttgag tgag 24

<210> SEQ ID NO 32
<211> LENGTH: 24
<212> TYPE: DNA
<213> ORGANISM: Artificial Sequence
<220> FEATURE:
<223> OTHER INFORMATION: PCR primer

<400> SEQUENCE: 32
cttttgcctg gtaagtgctc atgc 24

<210> SEQ ID NO 33
<211> LENGTH: 23
<212> TYPE: DNA
<213> ORGANISM: Artificial Sequence
<220> FEATURE:
<223> OTHER INFORMATION: PCR primer

<400> SEQUENCE: 33
ctgcatttca gaggtcccca atg 23

<210> SEQ ID NO 34

-continued

```
<211> LENGTH: 22
<212> TYPE: DNA
<213> ORGANISM: Artificial Sequence
<220> FEATURE:
<223> OTHER INFORMATION: PCR primer

<400> SEQUENCE: 34

ttaccacgag ctctgcccgc ag                                              22


<210> SEQ ID NO 35
<211> LENGTH: 20
<212> TYPE: DNA
<213> ORGANISM: Artificial Sequence
<220> FEATURE:
<223> OTHER INFORMATION: PCR primer

<400> SEQUENCE: 35

cctggctcac agtgtcagag                                                 20


<210> SEQ ID NO 36
<211> LENGTH: 20
<212> TYPE: DNA
<213> ORGANISM: Artificial Sequence
<220> FEATURE:
<223> OTHER INFORMATION: PCR primer

<400> SEQUENCE: 36

cagggctctc ctcgattttt                                                 20


<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37

ccctgctcgt ggtgaccgaa                                                 20


<210> SEQ ID NO 38
<211> LENGTH: 20
<212> TYPE: DNA
<213> ORGANISM: Artificial Sequence
<220> FEATURE:
<223> OTHER INFORMATION: PCR primer

<400> SEQUENCE: 38

gcaggctctc tttgatctgc                                                 20
```